US 7,459,468 B2
Dec. 2, 2008

(12) United States Patent
Haque et al.

(54) ARYL SULFONIC PYRIDOXINES AS ANTIPLATELET AGENTS

(75) Inventors: Wasimul Haque, Edmonton (CA); James Diakur, Winnipeg (CA)

(73) Assignee: Medicure International, Inc., West Indies (BB)

( * ) Notice: Subject to any disclaimer, the term of this patent is extended or adjusted under 35 U.S.C. 154(b) by 490 days.

(21) Appl. No.: 10/974,707

(22) Filed: Oct. 28, 2004

(65) Prior Publication Data

US 2006/0094748 A1    May 4, 2006

(51) Int. Cl.
*C07D 213/02* (2006.01)
*C07D 471/02* (2006.01)
*A61K 31/44* (2006.01)

(52) U.S. Cl. .................. 514/345; 514/302; 514/352; 514/357; 546/115; 546/290; 546/304; 546/329; 546/339

(58) Field of Classification Search ................. 546/290; 514/345
See application file for complete search history.

(56) References Cited

U.S. PATENT DOCUMENTS

| | | | |
|---|---|---|---|
| 3,206,463 A | 9/1965 | Baetz | |
| 3,227,721 A * | 1/1966 | Pfister, III et al. ........... 546/287 |
| 3,227,724 A | 1/1966 | Firestone et al. | |
| 3,282,778 A | 11/1966 | Lobel | |
| 3,632,806 A | 1/1972 | Ichizo et al. | |
| 3,910,921 A | 10/1975 | Esanu | |
| 3,987,177 A | 10/1976 | Giudicelli et al. | |
| 4,012,377 A | 3/1977 | Claisse et al. | |
| 4,032,534 A | 6/1977 | Chodkiewicz | |
| 4,036,844 A | 7/1977 | Thorne et al. | |
| 4,053,607 A | 10/1977 | Thorne et al. | |
| 4,137,316 A | 1/1979 | Esanu | |
| 4,167,562 A | 9/1979 | Evers | |
| 4,237,118 A | 12/1980 | Howard | |
| 4,361,570 A | 11/1982 | Fici | |
| 4,369,172 A | 1/1983 | Schor et al. | |
| 4,374,841 A | 2/1983 | Descamps et al. | |
| 4,515,771 A | 5/1985 | Fine | |
| 4,567,179 A | 1/1986 | Lombardino | |
| 4,569,938 A | 2/1986 | Esanu | |
| 4,569,939 A | 2/1986 | Esanu | |
| 4,581,363 A | 4/1986 | Esanu | |
| 4,605,741 A | 8/1986 | Zagnoli et al. | |
| 4,696,920 A | 9/1987 | Bentzen et al. | |
| 4,730,042 A | 3/1988 | Hege et al. | |
| 4,735,950 A | 4/1988 | Esanu | |
| 4,735,956 A | 4/1988 | Baldwin et al. | |
| 4,837,239 A | 6/1989 | Benjamin et al. | |
| 4,843,071 A | 6/1989 | Hohenwarter | |
| 4,898,879 A | 2/1990 | Madsen et al. | |
| 4,962,121 A | 10/1990 | Hamberger et al. | |
| 5,001,115 A | 3/1991 | Sloan | |
| 5,053,396 A | 10/1991 | Blass | |
| 5,118,505 A | 6/1992 | Költringer | |
| 5,130,311 A | 7/1992 | Guillaumet et al. | |
| 5,130,324 A | 7/1992 | Ulrich et al. | |
| 5,132,115 A | 7/1992 | Wolter et al. | |
| 5,155,116 A | 10/1992 | Guillaumet et al. | |
| 5,210,083 A | 5/1993 | Pfirrmann | |
| 5,213,813 A | 5/1993 | Kornecki et al. | |
| 5,254,557 A | 10/1993 | Buckle et al. | |
| 5,254,572 A | 10/1993 | Serfontein | |
| 5,272,165 A | 12/1993 | Ulrich et al. | |
| 5,278,154 A | 1/1994 | Lacoste et al. | |
| 5,288,716 A | 2/1994 | Speck | |
| 5,326,757 A | 7/1994 | Demopoulos | |
| 5,328,453 A | 7/1994 | Sibalis | |
| 5,372,999 A | 12/1994 | Schneider et al. | |
| 5,385,937 A | 1/1995 | Stamler et al. | |
| 5,420,112 A | 5/1995 | Lewis et al. | |
| 5,441,972 A | 8/1995 | Ogata et al. | |
| 5,504,090 A | 4/1996 | Neely | |
| 5,563,126 A | 10/1996 | Allen et al. | |
| 5,569,459 A | 10/1996 | Shlyankevich | |
| 5,569,648 A | 10/1996 | Lewis et al. | |
| 5,594,004 A | 1/1997 | Katano et al. | |
| 5,631,271 A | 5/1997 | Serfontein | |
| 5,633,228 A | 5/1997 | Lewis et al. | |
| 5,648,335 A | 7/1997 | Lewis et al. | |
| 5,728,684 A | 3/1998 | Cheng et al. | |
| 5,733,884 A | 3/1998 | Barbul et al. | |
| 5,733,916 A | 3/1998 | Neely | |

(Continued)

FOREIGN PATENT DOCUMENTS

BE    831350    1/1976

(Continued)

OTHER PUBLICATIONS

Doktorowa et al, Tetrahedron, 1969, vol. 25, No. 16, pp. 3527-3553.*

(Continued)

*Primary Examiner*—Zinna N Davis
(74) *Attorney, Agent, or Firm*—Brian R. Dorn; Merchant & Gould P.C.

(57) ABSTRACT

Aryl sulfonic pyridoxine compounds with antiplatelet aggregation characteristics for the treatment of cardiovascular and cardiovascular related disease, are described. The methods are directed to administering pharmaceutical compositions comprising aryl sulfonic pyridoxines.

36 Claims, No Drawings

U.S. PATENT DOCUMENTS

| | | | |
|---|---|---|---|
| 5,770,215 A | 6/1998 | Moshyedi | |
| 5,795,873 A | 8/1998 | Allen | |
| 5,804,163 A | 9/1998 | Gibby et al. | |
| 5,804,594 A | 9/1998 | Murad | |
| 5,833,998 A | 11/1998 | Biedermann et al. | |
| 5,834,446 A | 11/1998 | Dow et al. | |
| 5,840,685 A | 11/1998 | Fujii et al. | |
| 5,847,008 A | 12/1998 | Doebber et al. | |
| 5,858,017 A | 1/1999 | Demopulos et al. | |
| 5,859,051 A | 1/1999 | Adams et al. | |
| 5,874,420 A | 2/1999 | Pelleg | |
| 5,874,443 A | 2/1999 | Kiely et al. | |
| 5,888,514 A | 3/1999 | Weisman | |
| 5,944,020 A | 8/1999 | Markov et al. | |
| 6,043,259 A | 3/2000 | Dhalla et al. | |
| 6,051,587 A | 4/2000 | Dakashinamurti et al. | |
| 6,066,659 A | 5/2000 | Speck | |
| 6,121,249 A | 9/2000 | Weissman et al. | |
| 6,274,170 B1 | 8/2001 | Heibel et al. | |
| 6,323,188 B1 | 11/2001 | Weissman | |
| 6,339,085 B1 | 1/2002 | Haque | |
| 6,358,960 B1 | 3/2002 | Senokuchi et al. | |
| 6,417,204 B1 | 7/2002 | Haque | |
| 6,489,345 B1 | 12/2002 | Sethi | |
| 6,544,547 B2 | 4/2003 | Hageman | |
| 6,548,519 B1 | 4/2003 | Haque | |
| 6,586,414 B2 | 7/2003 | Haque et al. | |
| 6,605,612 B2 | 8/2003 | Haque | |
| 6,667,315 B2 | 12/2003 | Haque | |
| 6,677,356 B1 | 1/2004 | Sethi et al. | |
| 6,780,997 B2 | 8/2004 | Haque | |
| 6,861,439 B2 | 3/2005 | Haque et al. | |
| 6,867,215 B2 | 3/2005 | Haque | |
| 6,890,943 B2 | 5/2005 | Haque | |
| 6,897,228 B2 | 5/2005 | Haque | |
| 7,105,673 B2 | 9/2006 | Haque | |
| 7,115,625 B2 | 10/2006 | Sethi et al. | |
| 7,115,626 B2 | 10/2006 | Sethi et al. | |
| 7,125,889 B2 | 10/2006 | Sethi et al. | |
| 7,132,430 B2 | 11/2006 | Sethi et al. | |
| 7,144,892 B2 | 12/2006 | Sethi et al. | |
| 7,148,233 B2 | 12/2006 | Sethi et al. | |
| 7,230,009 B2 | 6/2007 | Haque et al. | |
| 2003/0114424 A1 | 6/2003 | Haque et al. | |
| 2004/0121988 A1 | 6/2004 | Haque et al. | |
| 2004/0171588 A1 | 9/2004 | Haque | |
| 2004/0186077 A1 | 9/2004 | Diakur et al. | |
| 2004/0235907 A1 | 11/2004 | Sethi | |
| 2005/0107443 A1 | 5/2005 | Haque | |
| 2006/0019929 A1 | 1/2006 | Friesen | |
| 2006/0035864 A1 | 2/2006 | Friesen | |
| 2006/0094749 A1 | 5/2006 | Haque et al. | |
| 2006/0094761 A1 | 5/2006 | Haque et al. | |
| 2006/0148763 A1 | 7/2006 | Friesen et al. | |
| 2006/0241083 A1 | 10/2006 | Diakur et al. | |
| 2007/0032456 A1 | 2/2007 | Friesen | |
| 2007/0060549 A1 | 3/2007 | Friesen | |
| 2007/0142270 A1 | 6/2007 | Haque et al. | |
| 2007/0149485 A1 | 6/2007 | Friesen | |
| 2007/0167411 A1 | 7/2007 | Reimer | |
| 2007/0243249 A1 | 10/2007 | Reimer | |
| 2007/0249562 A1 | 10/2007 | Reimer | |

FOREIGN PATENT DOCUMENTS

| | | |
|---|---|---|
| BE | 863754 | 5/1978 |
| CA | 933 522 | 9/1973 |
| CH | 561 183 | 4/1975 |
| DE | 24 61 742 A | 7/1976 |
| DE | 43 44 751 A1 | 6/1995 |
| EP | 0 121 036 A1 | 10/1984 |
| EP | 0 144 051 A2 | 6/1985 |
| EP | 0 270 026 A2 | 6/1988 |
| EP | 0 416 248 A2 | 3/1991 |
| EP | 0 891 719 A1 | 1/1999 |
| FR | 5552 M | 12/1967 |
| FR | 5801 M | 3/1968 |
| FR | 6453 M | 12/1968 |
| FR | 2101010 | 3/1972 |
| FR | 2255883 | 7/1975 |
| FR | 2428640 | 1/1980 |
| GB | 1 013 939 | 12/1965 |
| GB | 1 201 014 | 8/1970 |
| GB | 1 248 324 | 2/1972 |
| GB | 1 297 080 | 11/1972 |
| GB | 1 360 536 | 7/1974 |
| GB | 1 597 428 | 9/1981 |
| GB | 2 254 556 A | 10/1992 |
| JP | 48-21959 | 7/1973 |
| JP | 54-17130 | 2/1979 |
| JP | 10-158244 | 6/1998 |
| JP | 2000-26295 | 1/2000 |
| WO | WO 91/19500 | 12/1991 |
| WO | WO 94/18965 | 9/1994 |
| WO | WO 97/30047 | 8/1997 |
| WO | WO 98/28310 | 7/1998 |
| WO | WO 02/04421 A2 * | 1/2002 |
| WO | WO 02/34711 | 5/2002 |
| WO | WO 2005/060975 | 7/2005 |
| WO | WO 2005/070889 | 8/2005 |
| WO | WO 2006/005173 | 1/2006 |
| WO | WO 2006/026868 | 3/2006 |
| WO | WO 2006/056079 | 6/2006 |
| WO | WO 2006/058411 | 6/2006 |
| WO | WO 2006/102748 | 10/2006 |
| WO | WO 2006/136004 | 12/2006 |

OTHER PUBLICATIONS

Arbuzov, S., "Pharmacological Properties of the Products of the Condensation of Phenamine with Some Metabolites", *Farmakol. Toksikol*, vol. 31, No. 3, pp. 373-376 (1968) (Abstract only).

Aybak, M. et al., "Effect of Oral Pyridoxine Hydrochloride Supplementation on Arterial Blood Pressure with Essential Hypertension", *Drug Res.*, vol. 45, No. 12, pp. 1271-1273 (1995).

"B Vitamins May Cut Heart Disease Risk", *Harvard Health Letter*, 1 page (1998).

Baliga, B. et al., "Hyperhomocysteinemia in Type 2 Disbetes Mellitus: Cardiovascular Risk Factors and Effect of Treatment with Folic Acid and Pyridoxine", *Endocrine Practice*, vol. 6, No. 6, pp. 435-441 (Nov./Dec. 2000).

Barrett, S., "Homocysteine: A Cardiovascular Risk Factor Worth Considering", http://www.quackwatch.com/03HealthPromotion/homocysteine.html, 2 pages (1997).

Bennett, R. et al., "Vitamin $B_6$-Phosphonic Acids", *Journal of Medicinal and Pharmaceutical Chemistry*, vol. 1, No. 3, pp. 213-221 (1959).

Bernstein, A., "Vitamin $B_6$ in Clinical Neurology", *Annals of New York Academy of Sciences*, vol. 585, pp. 250-260 (1990).

Berger, A.R. et al., "Dose response, coasting, and differential fiber vulnerability in human toxic neuropathy: A prospective study of pyridoxine neurotoxicity", *Neurology*, vol. 42, No. 7, pp. 1367-1370 (Jul. 1992).

Bhagavan, H. et al., "Effect of Postweanling Pyridoxine Deficiency on Growth and Concentration of the Coenzyme Pyridoxal-5'-phosphate in Heart, Kidneys, Lungs, and Adrenals in Rats", *Rediat. Res.*, vol. 10, pp. 730-732 (1976).

Bode, W. et al., "Pyridoxal-5'-Phosphate and Pyridoxal Biokinetics in Male Wistar Rats Fed Graded Levels of VItamin B-6", *J. Nutr.*, vol. 121, No. 11, pp. 1738-1745 (Nov. 1991).

Brass, 2003, "Thrombin and platelet activation," *Chest*, 124: 18S-25S.

Buffon et al., 2002, "Widespread coronary inflammation in unstable angina," *N. Engl. J. Med.*, 347: 5-12.

Chasan-Taber, L. et al., "A Prospective Study of Folate and Vitamin $B_6$ and Risk of Myocardial Infarction in US Physicians", *Journal of the American College of Nutrition*, vol. 15, No. 2, pp. 136-143 (Apr. 1996).

Chen et al., 1994, "Thrombin receptor activation," *J. Biol. Chem.*, 269: 16041-16405.

Cho, Y. et al., "In Vivo Evidence for a Vitamin B-6 Requirement in Carnitine Synthesis", *J. Nutr.*, vol. 120, pp. 258-265 (1990).

Chung et al., 2002, "Mechanisms of action of proteinase-activated receptor agonists on human platelets," *Br. J. Pharmacol.*, 135: 1123-1132.

Ebadi, M. et al., "Convulsant Activity of Pyridoxal Sulphate and Phosphonoethyl Pyridoxal: Antagonism by GABA and its Synthetic Analogues", *Neuropharmacology*, vol. 22, No. 7, pp. 865-873 (1983).

Ellis, J. et al., "Prevention of Myocardial Infaction by Vitamin $B_6$", *Res. Commun. Molec. Pathol. Pharmacol.*, vol. 89, No. 2, pp. 208-220 (Aug. 1995).

Esmon, 2001, "Role of coagulation inhibitors in inflammation," *Thromb. Haemost.*, 86: 51-56.

Fitzgerald, 2001, "Vascular biology of thrombosis," *Neurology*, 57: S1-S4.

Folsom, A. et al., "Clinical Investigation and Reports: Prospective Study of Coronary Heart Disease Incidence in Relation to Fasting Total Homocysteine, Related Genetic Polymorphisms, and B Vitamins: The Atherosclerosis Risk in Communities (ARIC) Study", *Circulation*, vol. 98, pp. 204-210 (Jul. 21, 1998).

Fonda, M., "Interaction of Pyridoxal Analogues with Glutamate Apodecarboxylase and Asparate Apoaminotransferase", *The Journal of Biological Chemistry*, vol. 246, No. 7, pp. 2230-2240 (Apr. 10, 1971).

Gundermann, K. et al., "Oligomere von 5-Amino-8-vinylphthalazin-1,4(2H,3H)-dion", *Liebigs Ann. Chem.*, vol. 1979, No. 8, pp. 1657-1664 (Aug. 1979).

Harada, K. et al., "Studies on Vitamin $B_6$. (IV) Behavior of Pyridoxal Acylates in the Body After Parenteral Administration", *Vitamins Journal of the Vitamin Society of Japan*, vol. 45, No. 2, pp. 69-75 (Feb. 1972).

Hathcock, J., "Vitamins and minerals: efficacy and safety", *Am J Clin Nutr*, vol. 66, pp. 427-437 (1997).

Hayakawa, M. et al., "The In Vitro and In Vivo Inhibition of Protein Glycosylation and Diabetic Vascular Basement Membrane Thickening by Pyridoxal-5'-Phosphate", *J. Nutr. Sci. Vitaminol.*, vol. 37, pp. 149-159 (1991).

Heemskerk et al., 2002, "Platelet activation and blood coagulation," *Thromb. Haemost.*, 88: 186-193.

Hoover, D.M. et al., "Ultrastructural Lesions of Pyridoxine Toxicity in Beagle Dogs", *Vet. Pathol.*, vol. 18, pp. 769-777 (1981).

Kamalitsky, I., "Comparative Biochemical Characteristics of $B_6$-Vitamin Deficiency Caused by Alimentary Insufficiency of Pyridoxine and Isonicotinylhydrazine", *BOnPOCbI*. vol. 3, pp. 44-46 (1971).

Kim, Y. et al., "Synthesis and Structure-Activity Relationships of Pyridoxal-6-arylazo-5'-phosphate and Phosphonate Derivatives as P2 Receptor Antagonists", *Drug Development Research*, vol. 45, pp. 52-66 (1998).

Kok, F. et al., "Low Vitamin $B_6$ Status in Patients with Acute Myocardial Infarction", *Am. J. Cardiol.*, vol. 63, pp. 513-516 (Mar. 1, 1989).

Korytnyk, W., "Pyridoxine Chemistry. VI. Homologs of Pyridoxol and of 5-Pyridoxic Acid", *J. Am. Chem. Soc.*, vol. 8, pp. 112-115 (Jan. 1965).

Korytnyk et al., Schiff Bases of Pyriodoxal: Their Structure and the Stabilization of their Ring-Chain Tautomeric Forms by Acylation, Tetrahedron, 26 (23), 5415-25 (1970).

Korytnyk, W. et al., "Synthesis and Antagonist Properties of Pyridoxal Analogs Modified in the 5 Position", *J. Am. Chem. Soc.*, vol. 10, pp. 345-350 (May 1967).

Krinke, G. et al., "Pyridoxine Megavitaminosis: An Analysis of the Early Changes Induced with Massive Doses of Vitamin $B_6$ in Rat Primary Sensory Neurons", *J. Neuropathol. Exp. Neurol.*, vol. 44, No. 7, pp. 117-129 (Mar. 1985).

Kubyshkin, V. et al., "Comparative characteristics of the arrhythmic syndrome and the possibility for its coenzyme correction in dilated and hypertrophic cardiomyopathy", *Ter. Arkh.* 61(9): 82-85 (1989).

Kunapuli et al., 2003, "Platelet purinergic receptors," *Curr. Opin. Pharmacol.*, 3: 175-180.

Lal, K. et al., "Hypotensive action of 5-HT receptor agonists in the vitamin $B_6$-deficient hypertensive rat", *Eur. J. Pharmacol.*, vol. 234, Nos. 2/3, pp. 183-189 (Apr. 1993).

Lal, K. et al., "Calcium channels in vitamin $B_6$ deficiency-induced hypertension", *Journal of Hypertension*, vol. 11, No. 12, pp. 1357-1362 (Dec. 1993).

Lal, K. et al., "The effect of vitamin $B_6$ on the systolic blood pressure of rats in various animal models of hypertension", *Journal of Hypertension*, vol. 14, No. 3, pp. 355-363 (Mar. 1996).

Levy, H. et al., "Pyridoxine Deficiency in Congestive Heart Failure", *P.S.E.B.M.*, vol. 101, pp. 617-621 (1959).

Manore, M. et al., "Changes In Plasma Pyridoxal Phosphate (PLP) In Diabetic (D), Hypertensive (HTN) and Hypertensive-diabetic (HTN-D) Men Fed A Constant Vitamin B-6 (B6) Diet", *FASEB J*, Abstract 1254 (1991).

Markov, A. et al, "Hemodynamic, electrocardiographic, and metabolic effects of fructose diphosphate on acute myocardial ischemia", *American Heart Journal*, vol. 100, No. 5, pp. 639-646 (Nov. 1980).

Medicure brochure, "Pyridoxine as a Template for the Design of Novel Anti-Platelet Agents," 1 page (Date Unknown).

Mendelsohn, A. et al., "Hemodynamic and Clinical Effects of Oral Levodopa in Children With Congestive Heart Failure", *JACC*, vol. 30, No. 1, pp. 237-242 (Jul. 1997).

Merrill, Jr. et al. A. et al., "Diseases assocaited with defects in vitamin $B_6$ metabolism or utilization", *Ann. Rev. Nutr.*, vol. 7, pp. 137-156 (1987).

Miura, R. et al., "Reactions of Phosphonate Analogs of Pyridoxal Phosphate with Apo-aspartate Aminostransferase", *Archives of Biochemistry and Biophysics*, vol. 270, No. 2, pp. 526-540 (May 1, 1989).

Mulvaney, D. et al., "Electrocardiographic changes in vitamin $B_6$ deficient rats", *Cardiovascular Research*, vol. 13, pp. 506-513 (1979).

Nair, A. et al., "Effect of Pyridoxine and Administration on Brain Glutamate Dehydrogenase Activity and Blood Glucose Control in Strepto/otocin-Induced Diabetic Rats", *Biochimica et Biophysica Acta*, vol. 1381, pp. 351-354 (1998).

Nystedt et al., 1994, "Molecular cloning of a potential proteinase activated receptor," *Proc. Natl. Acad. Sci. USA*, 91: 9208-9212.

Omenn, G. et al., "Preventing Coronary Heart Disease", *Circulation*, vol. 97, pp. 421-424 (1998).

Onorato, J. et al., "Pyridoxamine, an Inhibitor of Advanced Glycation Reactions, Also Inhibits Advanced Lipoxidation Reactions", *The Journal of Biological Chemistry*, vol. 275, No. 28, pp. 21177-21184 (Jul. 14, 2000).

Pasechnik, I., "Effect of Pyridoxine on the Blood Sugar Level Normally and During Experimental Hyperglycemia", *Vop. Pitan.*, vol. 30, No. 3, pp. 44-46 (Abstract only from *Chemical Abstracts—Pharmacodynamics*, vol. 75 No. 9, p. 293 (Aug. 30, 1971)).

Patrono, C., "Aspirin: New Cardiovascular Uses for an Old Drug," *The American Journal of Medicine*, vol. 110, pp. 62S-65S (Jan. 8, 2001).

Paulose, C. et al., "Sympathetic Stimulation and Hypertension in the Pyridoxine-Deficient Adult Rat", *Hypertension*, vol. 11, No. 4, pp. 387-391 (Apr. 1988).

Rao, R. et al., "Failure of Pyridoxine to Improve Glucose Tolerance in Diabetics", *Journal of Clinical Endocrinology & Metabolism*, vol. 50, No. 1, pp. 198-200 (Jan. 1980).

Rao et al., 2000, "Congenital disorders of platelet transduction," *Arterioscler. Thromb. Vasc. Biol.*, 20: 285-289.

Rauch et al., 2001, "Thrombus formation on atherosclerotic plaques: pathogenesis and clinical consequences," *Ann. Intern. Med.*, 134: 224-238.

Rimm, E. et al., "Folate and Vitamin $B_6$ From Diet and Supplements in Relation to Risk of Coronary Heart Disease Among Women", *JAMA*, vol. 279, No. 5, pp. 359-364 (Feb. 4, 1998).

Sakuragi, T. et al., "The Synthesis of Long Chain Fatty Acid Derivatives of the Vitamin $B_6$ Group", *J. Am. Chem. Soc.*, vol. 78, pp. 839-842 (Feb. 20, 1956).

Sasaki, H. et al., "Effect of Pyridoxal Phosphate on the Carbohydrate and Lipid Metabolism of the Patient with Diabetes Mellitus", *Niigata Igakkai Zasshi*, vol. 85, No. 3, pp. 163-169 (1971). (Abstract provided in English).

Savage et al., 2001, "Mechanisms of platelet aggregation," *Curr. Opin. Hematol.*, 8: 270-276.

Sethi, R. et al., "Differential changes in left and right ventricular adenylyl cyclase activities in congestive heart failure", *The American Physiological Society*, vol. 272, No. 2, Part 2 of Two Parts, pp. H884-H893 (Feb. 1997).

Sethi, R. et al., "Inotropic Responses to Isoproterenol in Congestive Heart Failure Subsequent to Myocardial Infarction in Rats", *Journal of Cardiac Failure*, vol. 1, No. 5, pp. 391-399 (Dec. 1995).

Sexton, R. Jr., Abstract, 1 page, "Aspirin in cardiovascular disease," *Tenn. Med.*, vol. 94, No. 6, pp. 208-210 (Jun. 2001).

Stirtan, W. et al., "Phosphonate and $\alpha$-Fluorophosphonate Analogue Probes of the Ionization State of Pyridoxal 5'-Phosphate (PLP) in Glycogen Phosphorylase", *Biochemistry*, vol. 35, pp. 15057-15064 (1996).

Takuma, Y. et al., "Combination Theory of Infantile Spasms With High-Dose Pyridoxal Phosphate and Low-Dose Corticotropin", *Journal of Child Neurology*, vol. 11, No. 1, pp. 35-40 (Jan. 1996).

Tanaka, T. et al., "Pyridoxine Derivatives", *Chemical Abstracts*, vol. 62, No. 12, 1 page (Jun. 7, 1965).

Tomita, I. et al., "Synthesis of Vitamin $B_6$ Derivatives. II 3-Hydroxy-4-Hydroxymethyl-2-Methyl-5-Pyridine Acetic Acid and Related Substances", *J. Heterocyclic Chemistry.*, vol. 3, pp. 178-183 (Jun. 1966).

Trezise, D. et al., "$P_2$ purinoceptor antagonist properties of pyridoxal-5-phosphate", *Eur. J. Pharmacol.*, vol. 259, No. 3, pp. 295-300 (Jul. 11, 1994).

Vanderjagt, D. et al., "Vitamin $B_6$ Status in a Healthy Elderly Population", *Annals New York Academy of Sciences*, pp. 562-564 (date unknown).

Verhoef, P. et al., "A Common Mutation in the Methylenetetrahydrofolate Reductase Gene and Risk of Coronary Heart Disease: Results Among U.S. Men", *JACC*, Vo. 32, No. 2, pp. 353-359 (Aug. 1998).

Verhoef, P. et al., "Homocysteine Metabolism and Risk of Myocardial Infarction: Relation with Vitamins $B_6$, $B_{12}$, and Folate", *Am. J. Epidemiol.*, vol. 143, No. 9, pp. 845-859 (May 1, 1996).

Vernaak, W.J.H. et al., "Vitamin $B_6$ and coronary artery disease. Epidemiological observations and case studies", *Atherosclerosis*, vol. 63, pp. 235-238 (Feb. 1987).

Vidrio, H., "Interaction with Pyridoxol as a Possible Mechanism of Hydralazine Hypotension", *Journal of Cardiovascular Pharmacology*, vol. 15, pp. 150-156 (1990).

Viscontini, V. et al., "Über einige Derivate des Pyridoxals", *Helvetica Chimica Acta*, vol. 34, No. 296, pp. 2438-2439 (1951).

Vu et al., 1991, "Molecular cloning of a function thrombin receptor reveals a novel proteolytic mechansim of receptor activation," *Cell*, 64: 1057-1068.

Windebank, A., "Neurotoxicity of Pyridoxine Analogs Is Related to Coenzyme Structure", *Neurochemical Pathology*, vol. 3, pp. 159-167 (1985).

Yamagata, S. et al., "Therapeutic Effects of Pyridoxal Phosphate on Diabetic Neuropathy", *Bitamin*, vol. 35, No. 6, pp. 485-493 (1967). (Abstract provided in English).

Yan, S. et al., "A Role for Pyridoxal Phosphate in the Control of Dephosphorylation of Phosphorylase $\alpha$", *The Journal of Biological Chemistry*, vol. 264, No. 17, pp. 8263-8269 (1979).

Yarat, A. et al., "Effect of vitamin B6 on lenses of diabetic rats", *Indian Journal of Experimental Biology*, vol. 36, pp. 1269-1272 (Dec. 1998).

Zempleni, J. et al., "The utilization of intravenously infused pyridoxine in humans", *Clinica Chimica Acta*, vol. 229, Nos. 1, 2, pp. 27-36 (Sep. 1994).

Zhang, W., et al., "Pyridoxine as a template for the design of antiplatelet agents", Bioorganic & Medicinal Chemistry Letters, 14: 4747-4750 (2004).

Califf et al., 1998, "Myonecrosis after revascularization procedures", *J. Am. Coll. Cardiol.* 31: 241-251.

ESPRIT investigators, 2000, "Novel dosing regimen of eptifibatide in planned coronary stent implantation (ESPRIT): a randomised, placebo-controlled trial", Lancet 356: 2037-2044.

Bertrand et al. "Double-Blind Study of the Safety of Clopidogrel With and Without a Loading Dose in Combination With Aspirin Compared with Ticlopidine in Combination With Aspirin after Coronary Stenting" Circulation, Aug. 8, 2000. 102: 624-629.

Gilchrist et al. "Pharmacodynamics andPharmacokinetics of Higher -Dose, Double Bolus Eptifibatide in Percutaneous Coronary Intervention" Circulation Jul. 24, 2001 104: 406-411.

Harrington et al. "A possible mechanism for the inhibiting of blood platelet aggregation by pyridoxal-5'-phosphate" Biochemical Society Transactions (1996) 24: 76S.

Kambayashi et al. "Cilostazol as a Unique Antithrombotic Agent" Current Pharmaceutical Design 2003, 9: 2289-2302.

Nolan et al. "Effect of Pyridoxal-5'-phosphate on aggregation of platelets from stored human concentrates induced by arachidonic acid" Biochemical Society Transactions (1996) 24: 95S.

Popma et al. "Antithrombotic Therapy in Patients Undergoing Coronary Angioplasty" Chest 1998; 114: 728S-741S.

Sharis et al. "The Antiplatelet Effect of Ticlopidine and Clopidogrel" Annals of Internal Medicine vol. 129, Issue 5, Sep. 1, 1988, p. 394-405.

Tcheng "Perspectives on the Future of Platelet Glycoprotein llb/llla Blockade Therapy" Texas Heart Institute Journal vol. 25, No. 1 (1998) p. 49-56.

Tsutsui et al. "Effect of Cilostazol, a Novel Anti-Platelet Drug, on Restenosis After Percutaneous Transluminal Coronary Angioplasty" Japan Circulation Journal 1996; vol. 60: 207-215.

Weltermann et al. "Effects of pretreatment with clopidogrel on platelet and coagulation activation in patients undergoing elective coronary stenting" Thrombosis Research 112 (2003) p. 19-24.

Wyk et al. "The In Vivo effect in humans of pyridoxal-5'-phosphate on platelet function and blood coagulation" Thrombosis Research 66: 657-668, (1992).

Diakur et al., "Pyridoxine as a template for the design of novel anti-platelet agents", Abstracts of Papers, 226th ACS National Meeting, New York, NY, United States, Sep. 7-11, 2003, MEDI-328, American Chemical Society, Washington, D.C. (English) (2003).

* cited by examiner

ARYL SULFONIC PYRIDOXINES AS ANTIPLATELET AGENTS

FIELD OF THE INVENTION

This invention relates to aryl sulfonic pyridoxines and methods of treating cardiovascular, cerebrovascular, and cardiovascular related diseases or symptoms by administering pharmaceutical compositions comprising an aryl sulfonic pyridoxine.

BACKGROUND

Thrombosis, the development of blood clots within arterial vessels, is due to a complex mechanism involving the activation of both platelet aggregation and the coagulation protease cascade (*Ann. Intern Med.* (2001) 134: 224-38; *N. Engl. J. Med.* (2002) 347: 5-12; *Thromb. Haemost.* (2002) 86: 51-6). The pathways involved normally inhibit blood loss after vessel injury, but in thrombosis and related conditions, these reactions are inappropriately initiated and propagated.

On the molecular level, thrombosis is initiated by the release of mediators such as tissue factor (TF), von Willebrand Factor (vWF) (*J. Thromb. Haemost.* (2003) 1: 1602-1612), and collagen from ruptured atherosclerotic plaques or from damaged blood vessels. Collagen and vWF bind to receptors on platelets and initiate their activation. Once activated, platelets release secretory granules containing ADP, ATP, and calcium (*Curr. Opin. Hematol.* (2001) 8: 270-276). Activated platelets also synthesize and release thromboxane. The released ADP and thromboxane bind to receptors on the platelets to further propagate platelet activation. Once platelets are activated they start aggregating to initiate clot formation.

TF and vWF also initiate the blood coagulation cascade, which consists of two separate pathways that converge on a common endpoint. Both pathways involve the serial activation of the serine protease clotting factors and ultimately lead to the activation of thrombin. Thrombin, once activated, cleaves fibrinogen to form fibrin. Thrombin, Factor Xa, and Factor VIIa can also activate platelets by cleaving the G protein-coupled protease-activated receptors PAR-1, PAR-3, and PAR-4 (*Chest* (2003) 124: 18S-25S). PAR-1, the prototype receptor, is activated following cleavage of its amino-terminal exodomain to produce a new amino-terminus (*Cell* (1991) 64: 1057-68). The new amino terminus then binds to the receptor to effect signaling (*J. Biol. Chem.* (1994) 269: 16041-45). PARs are therefore peptide receptors that contain their own ligand. PAR-2 is activated by trypsin and not by thrombin (*Proc. Natl. Acad. Sci. USA* (1994) 91: 9208-12).

Therefore, there is a need for compounds that inhibit the proteases of the blood and thus block platelet aggregation.

SUMMARY OF THE INVENTION

One embodiment of the invention includes aryl sulfonic pyridoxines, compositions containing the aryl sulfonic pyridoxines, and methods of treatment using therapeutically effective amounts of aryl sulfonic pyridoxines. Compounds and compositions of the invention can be used to treat cardiovascular, cerebovascular or related diseases and symptoms thereof.

The invention also provides an embodiment of the formula I:

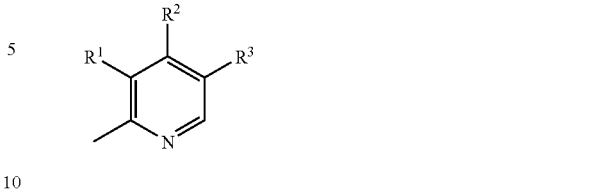

wherein
$R^1$ is —OH, —O-alkyl, —$(CH_2)_n$OH where n' is an integer from 1 to 8, alkyl, cycloalkyl, or O-alkyl-aryl-$R^4$, where $R^4$ is —CN or amidine;

$R^2$ is alkyl; —$(CH_2)_n$OH where n' is as defined above; —$(CH_2)_n$COOH where n is an integer from 0 to 8; —$(CH_2)_n$COO$(CH_2)_n$CH_3$ where n is as defined above; $(CH_2)_n$-aryl-$R^5$ where n is as defined above and $R^5$ is $SO_2NH_2$ or $SO_2NHC(CH_3)_3$; $(CH_2)_n$-aryl-aryl-$R^5$, where n and $R^5$ are as defined above, or —$(CH_2)_n$—NH-aryl-$R^5$, where n and $R^5$ are as defined above;

$R^3$ is —$(CH_2)_n$OH where n' is as defined above; $(CH_2)_n$—NH-aryl-$R^5$, where n and $R^5$ are as defined above; $(CH^2)_n$—NH—CO-aryl-$R^5$ where n and $R^5$ are as defined above; $(CH_2)_n$—NH-aryl-$R^5$ where n and $R^5$ are as defined above; $(CH_2)_n$—NH—CO-aryl-aryl-$R^5$ where n and $R^5$ are as defined above; and $R^1$ and $R^2$ when taken together form compounds of formula II,

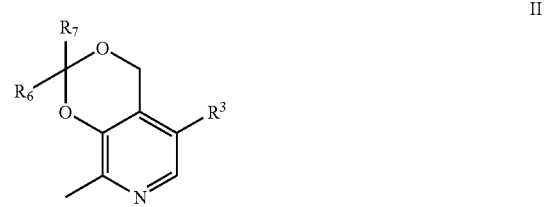

wherein $R^6$ and $R^7$ are independently H or $CH_3$;
or a pharmaceutically acceptable salt thereof.

DETAILED DESCRIPTION OF THE INVENTION

The invention provides compounds of the formula I:

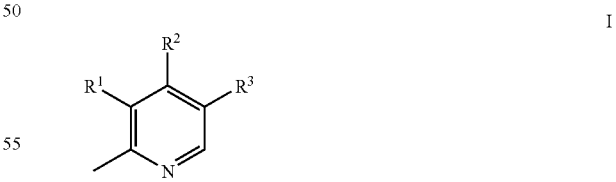

wherein
$R^1$ is —OH, —O-alkyl, —$(CH_2)_n$OH where n' is an integer from 1 to 8, alkyl, cycloalkyl, or O-alkyl-aryl-$R^4$, where $R^4$ is —CN or amidine;

$R^2$ is alkyl; —$(CH_2)_n$OH where n' is as defined above; —$(CH_2)_n$COOH where n is an integer from 0 to 8; —$(CH_2)_n$COO$(CH_2)_n$CH_3$ where n is as defined above; $(CH_2)_n$-aryl-$R^5$ where n is as defined above and $R^5$ is $SO_2NH_2$ or $SO_2NHC(CH_3)_3$; $(CH_2)_n$-aryl-aryl-$R^5$, where n and $R^5$ are as defined above, or $—(CH_2)_n—NH$-aryl-$R^5$, where n and $R^5$ are as defined above;

$R^3$ is $—(CH_2)_{n'}OH$ where n' is as defined above; $(CH_2)_n—NH$-aryl-$R^5$, where n and $R^5$ are as defined above; $(CH^2)_n—NH—CO$-aryl-$R^5$ where n and $R^5$ are as defined above; $(CH_2)_n—NH$-aryl-aryl-$R^5$ where n and $R^5$ are as defined above; $(CH_2)_n—NH—CO$-aryl-aryl-$R^5$ where n and $R^5$ are as defined above; and $R^1$ and $R^2$ when taken together form compounds of formula II,

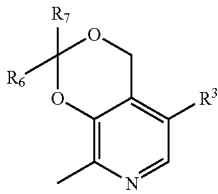

wherein $R^6$ and $R^7$ are independently H or $CH_3$;
or a pharmaceutically acceptable salt thereof.

The invention also provides an embodiment of the formula III:

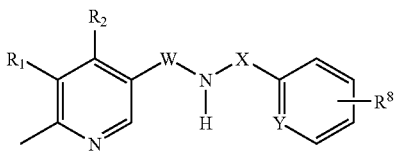

wherein
$R^1$ is OH, $OCH_3$, or $OCH_2$-(4-tert-Butyl-phenyl), or

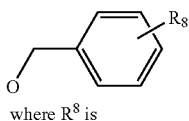

where $R^8$ is

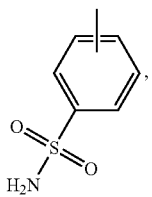 , 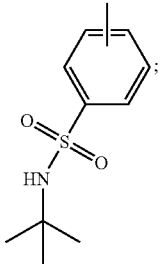 ;

$R^2$ is $CH_2OH$ or

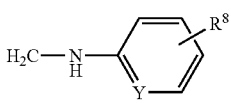

where $R^8$ is as defined above;
W is $(CH_2)_{n'}$ where n'=1, 2 or 3;
X is $(CH_2)_n$ where n=0, 1, 2, or 3, or C=O;

Y is C—H, C—F, or N; and
$R^1$ and $R^2$ when taken together form a compound of formula IV

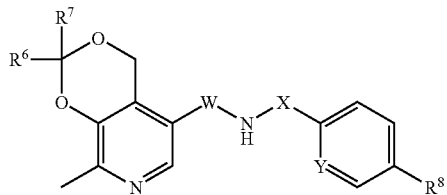

wherein $R^6$ and $R^7$ are as defined above;
or a pharmaceutically acceptable salt thereof.

As used herein "alkyl" includes a saturated linear or branched hydrocarbon radical. In one embodiment, alkyl has from 1 to 8 carbon atoms. In another embodiment, alkyl has from 1 to 6 carbon atoms. In another embodiment, alkyl has from 1 to 4 carbon atoms. In one embodiment, alkyl has 1 carbon. The alkyl group may optionally be substituted with one or more substituents such as fluorine, chlorine, alkoxy groups having from 1 to 8 carbon atoms (e.g., methoxy or ethoxy), or amido groups having from 1 to 8 carbon atoms, such as acetamido. These substituents may themselves be substituted with one or more functional groups such as hydroxy groups, carboxy groups, acetoxy groups, or halogens.

As used herein "cycloalkyl" refers to a saturated hydrocarbon having from 3 to 8 carbon atoms, preferably 3 to 6 carbon atoms, such as, for example, cyclopropyl, cyclopentyl, cyclohexyl, and the like.

As used herein "aryl" means a mono- or poly-nuclear aromatic hydrocarbon radical. Examples of "aryl" groups include, but are not limited to aromatic hydrocarbons such as a phenyl group or a naphthyl group. The aromatic group may optionally be substituted with one or more substituents such as fluorine, chlorine, alkyl groups having from 1 to 10 carbon atoms (e.g., methyl or ethyl), alkoxy groups having from 1 to 8 carbon atoms (e.g., methoxy or ethoxy), alkoxyalkyl groups having from 1 to 8 carbon atoms and one or more oxygen atoms, or amido groups having from 1 to 8 carbon atoms, such as acetamido. These substituents may themselves be substituted with one or more functional groups such as hydroxy groups, carboxy groups, acetoxy groups, or halogens.

In one embodiment, aryl is a phenyl group or a naphthyl group that is either unsubstituted or substituted.

In another embodiment, aryl is a heteroaryl in which one or more of the carbon atoms of an aromatic hydrocarbon is substituted with a nitrogen, sulfur, or oxygen. Examples of a "heteroaryl" include, but are not limited to pyridine, pyrimidine, pyran, dioxin, oxazine, and oxathiazine. Likewise, the heteroaryl may optionally be substituted with functional groups such as hydroxy groups, carboxy groups, halogens, and amino groups.

As used herein, "amidine" means a group having the formula

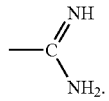

The invention also includes pharmaceutically acceptable salts of the compounds of the invention. The compounds of the invention are capable of forming both pharmaceutically acceptable acid addition and/or base salts. Pharmaceutically acceptable acid addition salts of the compounds of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and di-carboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine, etc. (see Berge et al., *J. Pharmaceutical Science*, 66: 1-19 (1977). The term "pharmaceutically acceptable salts" also includes any pharmaceutically acceptable base salt including, but not limited to, amine salts, trialkyl amine salts and the like. Such salts can be formed quite readily by those skilled in the art using standard techniques.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention. Base salts are formed with metals or amines, such as alkali and alkaline earth metals or organic amines. Examples of metals used as cations include, but are not limited to, sodium, potassium, magnesium, and calcium. Examples of suitable amines are N,N'-dibenzylethylenediamine, chloroprocaine, choline, diethanolamine, ethylenediamine, N-methylglucamine, and procaine.

Some of the compounds described herein contain one or more asymmetric centers and may thus give rise to enantiomers, diastereomers, and other stereoisomeric forms which may be defined in terms of absolute stereochemistry as (R)— or (S)—. The present invention is meant to include all such possible diastereomers and enantiomers as well as their racemic and optically pure forms. Optically active (R)— and (S)— isomers may be prepared using chiral synthons or chiral reagents, or resolved using conventional techniques. When the compounds described herein contain centers of geometric asymmetry, and unless specified otherwise, it is intended that the compounds include both E and Z geometric isomers. Likewise all tautomeric forms are intended to be included.

General Methods of Preparing Compounds of Formulae I, II, III, and IV

The compounds are generally prepared by combining an aldehyde or a carboxylate with an amine group to produce an elaborated pyridine structure. The general scheme of preparing the compounds of the formulae comprise protecting the hydroxyl groups at $R_1$ and $R_2$ of pyridoxine with known blocking groups such as esters, ethers, cyclic acetals, cyclic ketals, etc. and elaborating $R^3$ through generating an aldehyde, acid, halide, or amine functionality as shown in schemes 1-4. $R^3$ may be a nitro, amino, or cyano group that can be converted to an amidine by known chemical procedures. Additionally, protecting $R^1$ and $R^3$ with known blocking groups such as esters, ethers, cyclic acetals, cyclic ketals, etc. and elaborating $R^2$ through generating an aldehyde, acid, halide, or amine functionality can be achieved through the same general scheme as shown in Scheme 5.

Scheme 1

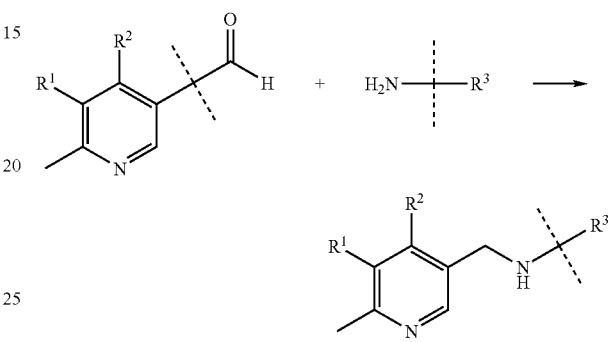

where the dashed lines are $(CH_2)_n$ where n = 0-8.

Scheme 2

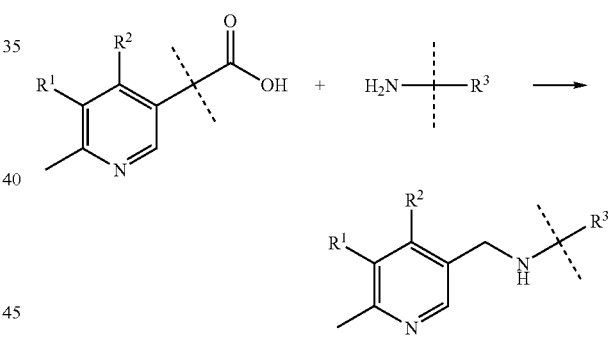

where the dashed lines are $(CH_2)_n$ where n = 0-8.

Scheme 3

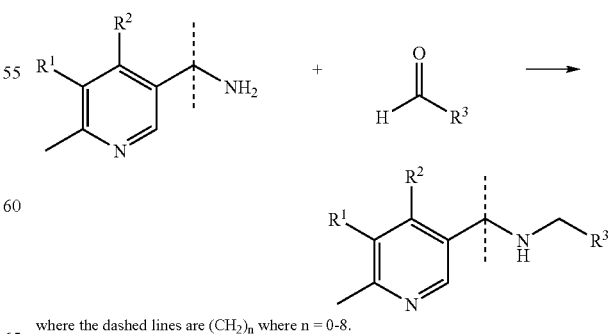

where the dashed lines are $(CH_2)_n$ where n = 0-8.

Scheme 4

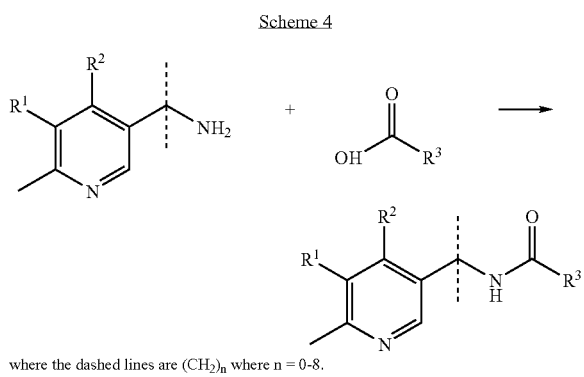

where the dashed lines are $(CH_2)_n$ where n = 0-8.

Scheme 5

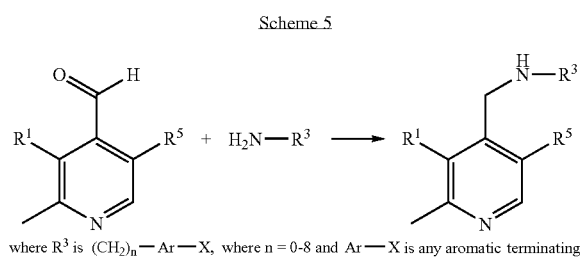

where $R^3$ is $(CH_2)_n$—Ar—X, where n = 0-8 and Ar—X is any aromatic terminating in —$SO_2NH_2$ or —$SO_2NH_2C(CH_3)_3$.

Other positions on the pyridoxine ring can also be substituted according to the aforementioned general scheme. Substitutions are not specific to the positions described above.

Conditions to be Treated

In one embodiment of the invention, compounds of the invention can be used to treat cardiovascular or related diseases. Cardiovascular or related diseases include, for example, cerebral ischemia, cerebral hemorrhage, ischemic stroke, hemorrhagic stroke, hypertension, myocardial infarction, ischemia reperfusion injury, myocardial ischemia, congestive heart failure, blood coagulation disorders, cardiac hypertrophy, and platelet aggregation. Cardiovascular or related diseases also include diseases that arise from thrombotic and prothrombotic states in which the coagulation cascade is activated such as, for example, deep vein thrombosis, disseminated intravascular coagulopathy, and pulmonary embolism.

Heart failure is a pathophysiological condition in which the heart is unable to pump blood at a rate commensurate with the requirement of the metabolizing tissues or can do so only from an elevated filling pressure (increased load). Thus, the heart has a diminished ability to keep up with its workload. Over time, this condition leads to excess fluid accumulation, such as peripheral edema, and is referred to as congestive heart failure.

When an excessive pressure or volume load is imposed on a ventricle, myocardial hypertrophy (i.e., enlargement of the heart muscle) develops as a compensatory mechanism. Hypertrophy permits the ventricle to sustain an increased load because the heart muscle can contract with greater force. However, a ventricle subjected to an abnormally elevated load for a prolonged period eventually fails to sustain an increased load despite the presence of ventricular hypertrophy, and pump failure can ultimately occur.

Heart failure can arise from any disease that affects the heart and interferes with circulation. For example, a disease that increases the heart muscle's workload, such as hypertension, will eventually weaken the force of the heart's contraction. Hypertension is a condition in which there is an increase in resistance to blood flow through the vascular system. This resistance leads to increases in systolic pressure, diastolic blood pressure, or both. Hypertension places increased tension on the left ventricular myocardium, causing it to stiffen and hypertrophy, and accelerates the development of atherosclerosis in the coronary arteries. The combination of increased demand and lessened supply increases the likelihood of myocardial ischemia leading to myocardial infarction, sudden death, arrhythmias, and congestive heart failure.

Ischemia is a condition in which an organ or a part of the body fails to receive a sufficient blood supply. When an organ is deprived of a blood supply, it is said to be hypoxic. An organ will become hypoxic even when the blood supply temporarily ceases, such as during a surgical procedure or during temporary artery blockage. Ischemia initially leads to a decrease in or loss of contractile activity. When the organ effected is the heart, this condition is known as myocardial ischemia, and myocardial ischemia initially leads to abnormal electrical activity. This can generate an arrhythmia. When myocardial ischemia is of sufficient severity and duration, cell injury can progress to cell death—i.e., myocardial infarction—and subsequently to heart failure, hypertrophy, or congestive heart failure.

Ischemic reperfusion of the organ occurs when blood flow resumes to an organ after temporary cessation. For example, reperfusion of an ischemic myocardium can counter the effects of coronary occlusion, a condition that leads to myocardial ischemia. Ischemic reperfusion to the myocardium can lead to reperfusion arrhythmia or reperfusion injury. The severity of reperfusion injury is affected by numerous factors, such as, for example, duration of ischemia, severity of ischemia, and speed of reperfusion. Conditions observed with ischemia reperfusion injury include neutrophil infiltration, necrosis, and apoptosis.

Pharmaceutical Compositions

Although it is possible for compounds of the invention to be administered alone in a unit dosage form, the compounds are typically administered in admixture with a carrier as a pharmaceutical composition to provide a unit dosage form. The invention provides pharmaceutical compositions containing at least one compound of the invention. A pharmaceutical composition comprises a pharmaceutically acceptable carrier in combination with a compound of the invention or a pharmaceutically acceptable salt of a compound of the invention.

A pharmaceutically acceptable carrier includes, but is not limited to, physiological saline, ringers, phosphate-buffered saline, and other carriers known in the art. Pharmaceutical compositions can also include additives such as, for example, stabilizers, antioxidants, colorants, excipients, binders, thickeners, dispersing agents, readsorpotion enhancers, buffers, surfactants, preservatives, emulsifiers, isotonizing agents, and diluents. Pharmaceutically acceptable carriers and additives are chosen such that side effects from the pharmaceutical compound are minimized and the performance of the compound is not canceled or inhibited to such an extent that treatment is ineffective.

Methods of preparing pharmaceutical compositions containing a pharmaceutically acceptable carrier in combination with a therapeutic compound of the invention or a pharmaceutically acceptable acid addition salt of a compound of the invention are known to those of skill in the art. All methods can include the step of bringing the compound of the invention in association with the carrier and additives. The formulations generally are prepared by uniformly and intimately bringing the compound of the invention into association with a liquid carrier or a finely divided solid carrier or both, and then, if necessary, shaping the product into the desired unit dosage forms.

For oral administration as a tablet or capsule, the compositions can be prepared according to techniques well known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or di-glycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Method of Treatment Using Compounds of The Invention

In another aspect of the invention, methods are provided for the treatment of cardiovascular or related diseases and symptoms thereof.

As used herein, the terms "treatment" and "treating" include inhibiting, alleviating, and healing cardiovascular or related diseases or symptoms thereof. Treatment can be carried out by administering a therapeutically effective amount of at least one compound of the invention. A "therapeutically effective amount" as used herein includes a prophylactic amount, for example an amount effective for alleviating or healing the above mentioned diseases or symptoms thereof.

A physician or veterinarian of ordinary skill readily determines a mammalian subject who is exhibiting symptoms of any one or more of the diseases described above. Regardless of the route of administration selected, a compound of the invention or a pharmaceutically acceptable acid addition salt of a compound of the invention can be formulated into pharmaceutically acceptable unit dosage forms by conventional methods known in the pharmaceutical art. An effective but nontoxic quantity of the compound is employed in treatment. The compounds can be administered in enteral unit dosage forms, such as, for example, tablets, sustained-release tablets, enteric coated tablets, capsules, sustained-release capsules, enteric coated capsules, pills, powders, granules, solutions, and the like. They can also be administered parenterally, such as, for example, subcutaneously, intramuscularly, intradermally, intramammarally, intravenously, and by other administrative methods known in the art.

The ordinarily skilled physician or veterinarian will readily determine and prescribe the therapeutically effective amount of the compound to treat the disease for which treatment is administered. In so proceeding, the physician or veterinarian could employ relatively low dosages at first, subsequently increasing the dose until a maximum response is obtained. Typically, the particular disease, the severity of the disease, the compound to be administered, the route of administration, and the characteristics of the mammal to be treated, for example, age, sex, and weight, are considered in determining the effective amount to administer. Administering a therapeutic amount of a compound of the invention for treating cardiovascular or related diseases or symptoms thereof, is in a range of about 0.1-100 mg/kg of a patient's body weight, more preferably in the range of about 0.5-50 mg/kg of a patient's body weight, per daily dose. The compound can be administered for periods of short and long duration. Although some individual situations can warrant to the contrary, short-term administration, for example, 30 days or less, of doses larger than 25 mg/kg of a patient's body weight is preferred to long-term administration. When long-term administration, for example, months or years, is required, the suggested dose usually does not exceed 25 mg/kg of a patient's body weight.

A therapeutically effective amount of a compound of the invention or a pharmaceutically acceptable addition salt of a compound of the invention for treating the above-identified diseases or symptoms thereof can be administered prior to, concurrently with, or after the onset of the disease or symptom. A compound of the invention can be administered concurrently. "Concurrent administration" and "concurrently administering" as used herein includes administering a compound of the invention and another therapeutic agent in admixture, such as, for example, in a pharmaceutical composition or in solution, or separately, such as, for example, separate pharmaceutical compositions or solutions administered consecutively, simultaneously, or at different times but not so distant in time such that the compound of the invention and the other therapeutic agent cannot interact and a lower dosage amount of the active ingredient cannot be administered.

In one embodiment of the invention, a method is provided for treating cardiovascular or related diseases comprising administering to a mammal a therapeutically effective amount of a compound of the invention or a pharmaceutically acceptable addition salt of a compound of the invention in a unit dosage form. The cardiovascular or related diseases that can be treated include hypertrophy, hypertension, congestive heart failure, heart failure subsequent to myocardial infarction, myocardial ischemia, cerebral ischemia, ischemia reperfusion injury, arrhythmia, myocardial infarction, blood coagulation, or platelet aggregation. Preferably, the cardiovascular disease treated is hypertrophy, congestive heart failure, arrhythmia, or ischemia reperfusion injury.

The compound of the invention can also be administered to treat cardiovascular diseases and other diseases that arise from thrombotic and prothrombotic states in which the coagulation cascade is activated, such as, for example, deep vein thrombosis, disseminated intravascular coagulopathy, Kasabach-Merritt syndrome, pulmonary embolism, myocardial infarction, stroke, thromboembolic complications of surgery, and peripheral arterial occlusion. A compound of the invention may also be useful in the treatment of adult respiratory distress syndrome, septic shock, septicemia, or inflammatory responses, such as edema and acute or chronic atherosclerosis, because thrombin has been shown to activate a large number of cells outside of the coagulation process, such as, for example, neutrophils, fibroblasts, endothelial cells, and smooth muscle cells.

The method for treating cardiovascular or related diseases can further comprise concurrent administration of other therapeutic agents already known to be suitable for treating the above-identified diseases. For example, methods of the invention include concurrently administering a compound of the invention or a pharmaceutically acceptable acid addition salt of a compound of the invention in combination with a therapeutic cardiovascular compound to treat hypertrophy, hypertension, congestive heart failure, heart failure subsequent to myocardial infarction, myocardial ischemia, ischemia reperfusion injury, arrhythmia, or myocardial infarction. Preferably, the cardiovascular disease treated is hypertrophy, congestive heart failure, arrhythmia, or ischemia reperfusion injury.

The compounds of the invention can also be used in combination with other therapeutic cardiovascular compounds that are generally used to treat cardiovascular or related diseases as well as symptoms thereof. A skilled physician or veterinarian readily determines a subject who is exhibiting symptoms of any one or more of the diseases described above and makes the determination about which compound is generally suitable for treating specific cardiovascular conditions and symptoms.

For example, myocardial ischemia can be treated by the administration of a compound of the invention or a pharmaceutically acceptable acid addition salt of a compound of the invention concurrently with another therapeutic agent. Other suitable therapeutic agents include, for example, a angiotensin converting enzyme inhibitor, an angiotensin II receptor antagonist, a calcium channel blocker, an antithrombolytic agent, a β-adrenergic receptor antagonist, a diuretic, an I-adrenergic receptor antagonist, or a mixture thereof.

As another example, congestive heart failure can be treated by the administration of a compound of the invention or a pharmaceutically acceptable acid addition salt of a compound of the invention concurrently with another therapeutic agent. Other suitable therapeutic agents include, for example, an angiotensin converting enzyme inhibitor, an angiotensin II receptor antagonist, a calcium channel blocker, a vasodilator, a diuretic, or a mixture thereof.

Myocardial infarction can be treated by the administration of a compound of the invention or a pharmaceutically acceptable acid addition salt of a compound of the invention concurrently with another therapeutic agent. Other suitable therapeutic agents include, for example, a angiotensin converting enzyme inhibitor, a calcium channel blocker, an antithrombolytic agent, a β-adrenergic receptor antagonist, a diuretic, an α-adrenergic receptor antagonist, or a mixture thereof.

Hypertension can be treated by the administration of a compound of the invention or a pharmaceutically acceptable acid addition salt of a compound of the invention concurrently with another therapeutic agent. Other suitable therapeutic agents include, for example, an angiotensin converting enzyme inhibitor, a calcium channel blocker, a β-adrenergic receptor antagonist, a vasodilator, a diuretic, an α-adrenergic receptor antagonist, or a mixture thereof.

Arrhythmia can be treated by the administration of a compound of the invention or a pharmaceutically acceptable acid addition salt of a compound of the invention concurrently with another therapeutic agent. Other suitable therapeutic agents include, for example, a calcium channel blocker, an β-adrenergic receptor antagonist, or a mixture thereof.

Blood clots in the arteries (arterial thrombosis) or veins (venous thrombosis) can be reduced or removed by the administration of a compound of the invention or a pharmaceutically acceptable acid addition salt of a compound of the invention concurrently with a anti platelet agent such as clopidogrel, aspirin, dipyridamole, etc., glycoprotein IIb/IIIa inhibitor such as INTEGRILIN® (eptifibatide) etc., or by anticoagulant such as UFH (unfractionated heparins) or LMWH (low molecular weight heparins) or by hirudin or argatroban etc.

Hypertrophy can be treated by the administration of a compound of the invention or a pharmaceutically acceptable acid addition salt of a compound of the invention concurrently with another therapeutic agent. Other suitable therapeutic agents include, for example, an angiotensin converting enzyme inhibitor, an angiotensin II receptor antagonist, a calcium channel blocker, or a mixture thereof.

Ischemia reperfusion injury can be treated by the administration of a compound of the invention or a pharmaceutically acceptable acid addition salt of a compound of the invention concurrently with another therapeutic agent. Other suitable therapeutic agents include, for example, an angiotensin converting enzyme inhibitor, an angiotensin II receptor antagonist, a calcium channel blocker, or a mixture thereof.

Compounds of the invention or pharmaceutically acceptable salts thereof can be administered post-surgically, alone or concurrently with other suitable therapeutic agents. For instance, the method would include, but is not limited to, administration to patients following hip replacement surgery, or invasive cardiovascular surgery, including coronary artery bypass graft (CABG), endarectomy, and heart valve replacement. Compounds of the invention or pharmaceutically acceptable salts thereof can be administered, alone or concurrently with other suitable therapeutic agents, following any angioplasty procedure. For instance, administration of said compounds may follow percutaneous transluminal angioplasty (PTA). PTA is used in coronary, pulmonary, peripheral, intracranial, extracranial carotid, renal, and aortic stenoses.

Additionally, medical devices can be coated with the compounds of the invention or pharmaceutically acceptable acid salts of the compound alone or in mixture with other suitable therapeutic agents (e.g., an angiotensin converting enzyme inhibitor). Medical devices that can be coated with the compounds of the invention or pharmaceutically acceptable salts thereof alone or in mixture with other suitable therapeutic agents include, but are not limited to, intravascular stents and catheters. Intravascular stents are used to prevent blood vessel wall collapse. Drug-eluting stents are coated with a mixture of polymers and drug to prevent restenosis. Examples of drug-eluting stents are the CYPHER™ sirolimus-eluting stent (Cordis Corp., Miami, Fla.) and TAXUS™ paclitaxel-eluting stent (Boston Scientific Corp., Natick, Mass.).

This invention is further characterized by the following examples. These examples are not meant to limit the scope of the invention but are provided for exemplary purposes to more fully describe the invention. Variation within the scope of the invention will be apparent to those skilled in the art.

EXAMPLES

All reagents used were purchased from standard commercial sources, or synthesized by known literature methods. HPLC analysis was performed using a Water 996 PDA High performance Liquid chromatograph equipped with a Water 600 controller. Signals were detected with a photodiode array detector (set at max plot 254-400 nm). NMR spectra were recorded on a Bruker AM-300 instrument ($^{13}$C, $^{19}$F and $^{31}$P at 75.5, 282 and 121 MHz respectively) and were calibrated using residual nondeuterated solvent as the internal reference. All $^{19}$F spectra are reported using hexafluorobenzene (δ−162.9 ppm) as the external standard while $^{31}$P spectra were collected using 85% $H_3PO_4$ (δ 0.0 ppm) as the external reference.

Example 1

Synthesis of 4'-[(2,2,8-Trimethyl-4H-[1,3]dioxino[4,5-c]pyridin-5-ylmethyl)-amino]-biphenyl-2-sulfonic acid tert-butylamide (1)

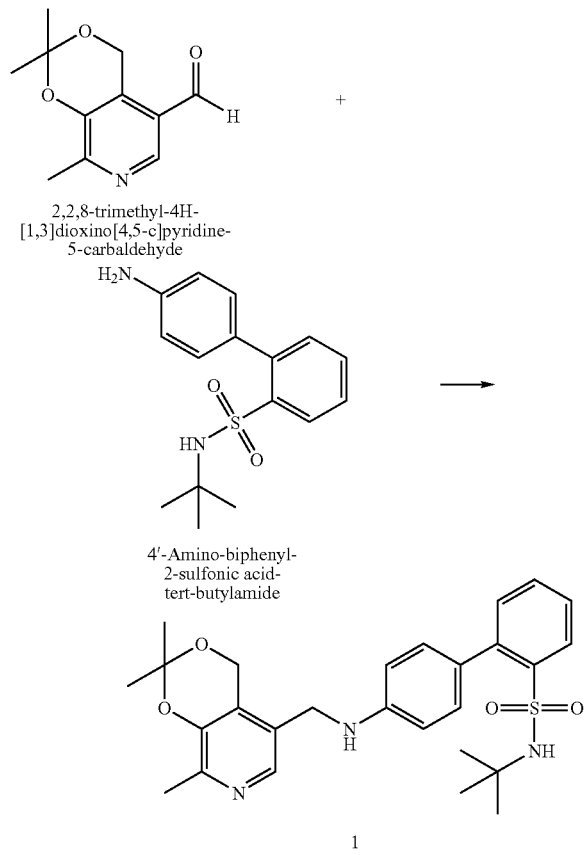

To a 250 mL three neck flask fitted with a condenser and Dean-Stark apparatus was added 4'-amino-biphenyl-2-sulfonic acid tert-butylamide (1.22 g, 4.0 mmol), p-toluenesulfonic acid monohydrate (152 mg, 0.8 mmol), 2,2,8-trimethyl-4H-[1,3]dioxino [4,5-c]pyridine-5-carbaldehyde (995 mg, 4.8 mmol) and toluene (120 ml). The reaction mixture was stirred at 120° C. under nitrogen atmosphere for 7 hours before concentrating to dryness. The resulting solid was then dissolved in acetic acid (20 mL), cooled to 0° C., followed by a slow addition of sodium borohydride (529 mg, 14 mmol). After the addition of sodium borohydride, dichloromethane (30 mL) was then added to the reaction mixture and stirring was continued at room temperature for an additional 3 hours. Sodium hydroxide (5 N) was added to neutralize the solution, and the reaction mixture was extracted with ethyl acetate, dried over MgSO$_4$, filtered and evaporated. The crude mixture was purified by column chromatography on silica gel using a mixture of ethyl acetate and hexane (1:1) as eluant, to give 4'-[(2,2,8-trimethyl-4H-[1,3]dioxino[4,5-c]pyridin-5-ylmethyl)-amino]-biphenyl-2-sulfonic acid tert-butylamide (1) (0.457 g, 24% yield) as a colorless solid.

$^1$H-NMR (CDCl$_3$): δ 8.13 (d, 1H), 8.04 (s, 1H), 7.52 (t, 1H), 7.41 (t, 1H), 7.35 (d, 2H), 7.28 (d, 1H), 6.70 (d, 2H), 4.90 (s, 2H), 4.20 (d, 2H), 3.99 (t, 1H), 3.69 (s, 1H), 2.41(s, 3H), 1.56 (s, 6H), 0.98 (s, 9H).

Example 2

Synthesis of 4'-[(5-Hydroxy-4-hydroxymethyl-6-methyl-pyridin-3-ylmethyl)-amino]-biphenyl-2-sulfonic acid tert-butylamide (2)

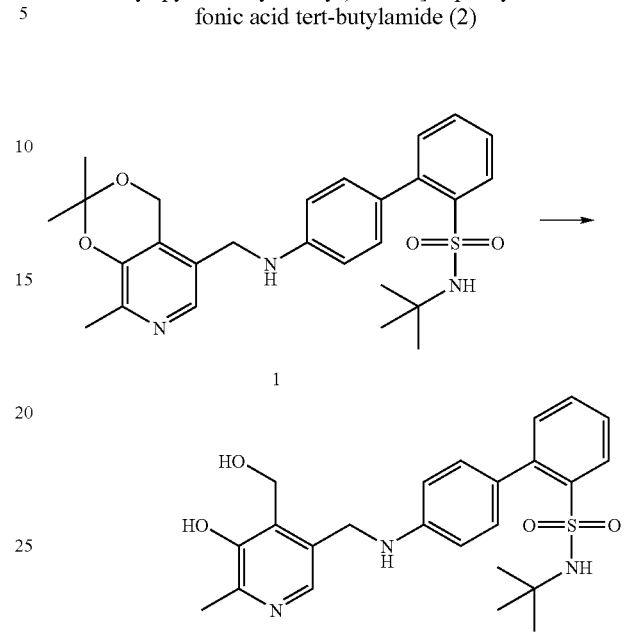

To a solution of 10% formic acid in water (50 mL) was added 3-[(2,2,8-trimethyl-4H-[1,3] dioxino [4,5-c]pyridin-5-ylmethyl)-amino]-benzonitrile (1) (336 mg, 0.7 mmol) and the reaction mixture was heated at 100° C. under nitrogen atmosphere. The reaction mixture was then concentrated to dryness. The resulting pale yellow solid was dissolved in small amount of dichloromethane and diethyl ether was added to induce precipitation of a yellow solid. The 4'-[(5-hydroxy-4-hydroxymethyl-6-methyl-pyridin-3-ylmethyl)-amino]-biphenyl-2-sulfonic acid tert-butylamide (2) (215 mg, 70% yield) was collected by filtration as a pale yellow solid.

$^1$H-NMR (DMSO-d$_6$): δ 8.70 (s, 1H), 8.07 (d, 1H), 7.77 (s, 1H), 7.60 (m, 2H), 7.43 (s, 4H), 7.33 (d, 1H), 5.14 (s, 2H), 4.77 (s, 2H), 2.33 (s, 3H), 0.98 (s, 9H).

Example 3

Synthesis of 4'-[(5-Hydroxy-4-hydroxymethyl-6-methyl-pyridin-3-ylmethyl)-amino]-biphenyl-2-sulfonic acid amide (3)

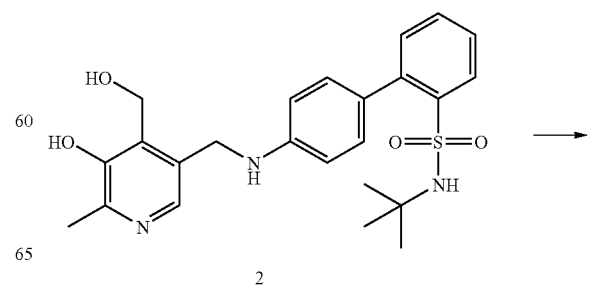

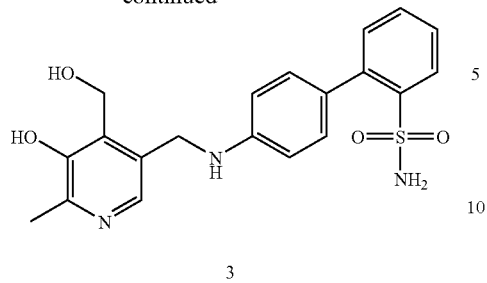

3

Hydrogen chloride gas was bubbled into a suspension of 4′-[(5-hydroxy-4-hydroxymethyl-6-methyl-pyridin-3-ylmethyl)-amino]-biphenyl-2-sulfonic acid tert-butylamide (2) (160 mg, 0.36 mmol) in methyl alcohol (20 mL) at 0° C. for 10 minutes. The solvent was evaporated and the products were purified on a silica gel column using a mixture of methyl alcohol:dichloromethane (1:9) as eluant to give 4′-[(5-hydroxy-4-hydroxymethyl-6-methyl-pyridin-3-ylmethyl)-amino]-biphenyl-2-sulfonic acid amide (3) (139 mg, 25% yield).

$^1$H-NMR (CD$_3$OD): δ 8.08 (d, 1H), 7.92 (s, 1H), 7.59 (t, 1H), 7.47 (t, 1H), 7.33 (d, 1H), 7.24 (d, 2H), 6.74 (d, 2H), 4.99 (s, 2H), 4.36 (s, 2H), 2.43 (s, 3H). MS m/z (ES$^+$): 400.22 (M+H$^+$).

Example 4

Synthesis of 2′-tert-Butylsulfamoyl-biphenyl-4-carboxylic acid (2,2,8-trimethyl-4H-[1,3]dioxino[4,5-c]pyridin-5-ylmethyl)-amide (4)

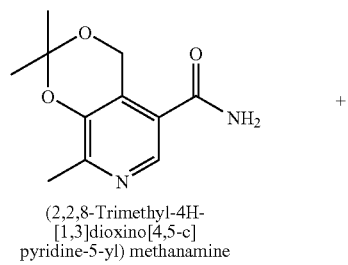

(2,2,8-Trimethyl-4H-[1,3]dioxino[4,5-c]pyridine-5-yl) methanamine

+

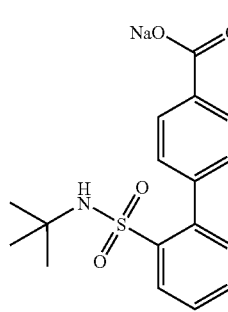

2′-Tert-butylsulfamoyl-biphenyl-4-carboxylic acid mono-sodium

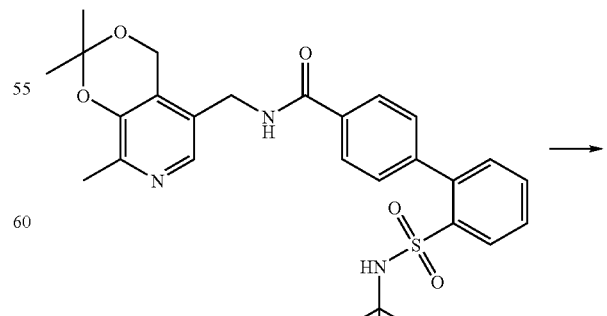

4

A mixture of 2′-tert-butylsulfamoyl-biphenyl-4-carboxylic acid mono-sodium salt (200 mg, 0.56 mmol), 2,2,8-trimethyl-4H-[1,3]dioxino[4,5-c]pyridin-5-yl)-methylamine (123 mg, 0.59 mmol), 1-[3-(dimethylamino)propyl]-3-ethyl carbodiimide hydrochloride(EDC) (226 mg, 1.18 mmol), and 4-(dimethylamino)pyridine (144 mg, 1.18 mmol) in anhydrous dichloromethane (25 mL) was stirred at room temperature under nitrogen atmosphere overnight. The reaction mixture was concentrated and the crude mixture was purified by column chromatography on silica gel using a mixture of methyl alcohol:dichloromethane (1:9) as eluant to give 2′-tert-butylsulfamoyl-biphenyl-4-carboxylic acid (2,2,8-trimethyl-4H-[1,3]dioxino[4,5-c]pyridin-5-ylmethyl)-amide (4) (196 mg, 67% yield) as a colorless solid.

$^1$H-NMR (CDCl$_3$): δ 8.16 (s, 1H), 8.04 (d, 1H), 7.94 (d, 2H), 7.57-7.46 (m, 5H), 5.01(s, 2H), 4.58 (d, 2H), 4.03 (s, 1H), 2.50 (s, 3H), 1.56 (s, 6H), 1.01 (s, 9H).

Example 5

Synthesis of 2′-tert-Butylsulfamoyl-biphenyl-4-carboxylic acid (5-hydroxy-4-hydroxymethyl-6-methyl-pyridin-3-ylmethyl)-amide (5)

4

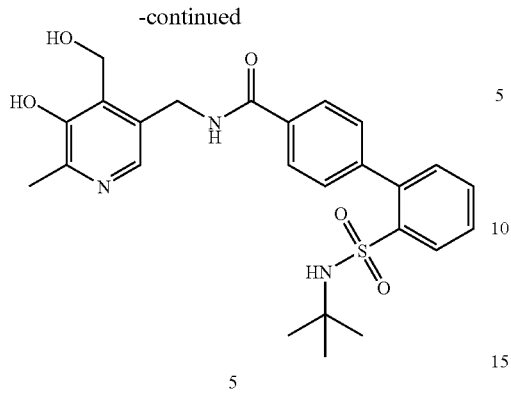

5

The hydrolysis of 2'-tert-butylsulfamoyl-biphenyl-4-carboxylic acid (2,2,8-trimethyl-4H-[1,3]dioxino[4,5-c]pyridin-5-ylmethyl)-amide (4) (300 mg, 0.57 mmol), following the procedure described in Example 2, gave 2'-tert-butylsulfamoyl-biphenyl-4-carboxylic acid (5-hydroxy-4-hydroxymethyl-6-methyl-pyridin-3-ylmethyl)-amide (5) (219 mg, 79% yield) as a colorless solid.

¹H-NMR (CD₃OD): δ 8.32 (m, 4H), 8.16 (s, 1H), 8.09 (d, 2H), 7.84 (t, 1H), 7.75 (d, 3H), 7.54 (d, 1H), 5.23 (s, 2H), 4.84 (s, 2H), 2.66 (s, 3H), 1.25 (s, 9H). MS m/z (ES⁺): 484.41 (M+H⁺).

Example 6

Synthesis of 2'-Sulfamoyl-biphenyl-4-carboxylic acid (5-hydroxy-4-hydroxymethyl-6-methyl-pyridin-3-ylmethyl)-amide (6)

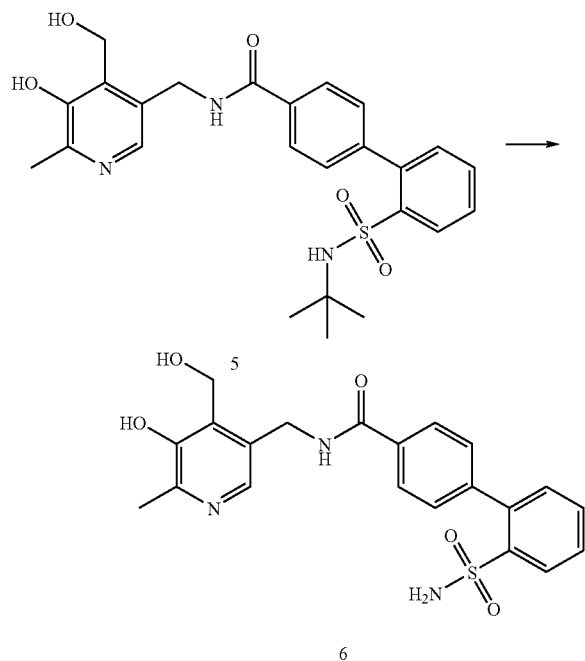

The hydrolysis of 2'-tert-butylsulfamoyl-biphenyl-4-carboxylic acid (5-hydroxy-4-hydroxymethyl-6-methyl-pyridin-3-ylmethyl)-amide (5) (101 mg, 0.21 mmol), following the procedure described in Example 3, gave 2'-sulfamoyl-biphenyl-4carboxylic acid (5-hydroxy-4-hydroxymethyl-6-methyl-pyridin-3-ylmethyl)-amide (6) (219 mg, 79% yield) as a colorless solid.

¹H-NMR (CD₃OD): δ 8.27 (m, 2H), 8.05 (d, 2H), 7.81-7.72 (m, 2H), 7.68 (d, 2H), 7.48 (d, 1H), 5.35 (s, 2H), 4.85 (s, 2H), 2.78 (s, 3H). MS m/z (ES⁺): 428.29 (M+H⁺).

Example 7

Synthesis of 4'-[(3-Hydroxy-5-hydroxymethyl-2-methyl-pyridin-4-ylmethyl)-amino]-biphenyl-2-sulfonic acid tert-butylamide (7)

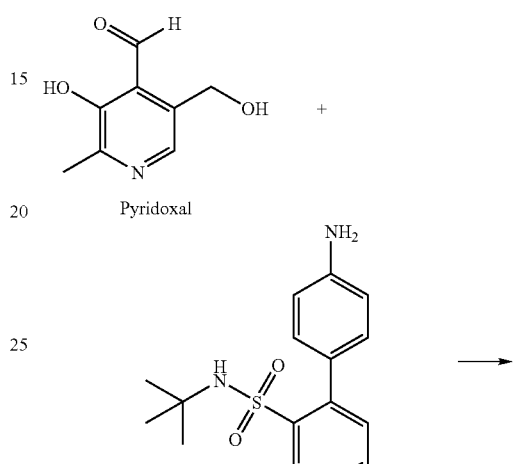

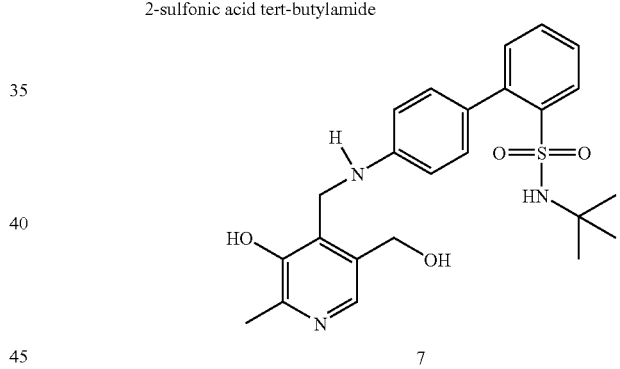

In a 250 mL three-necked round bottom flask fitted with a condenser and a Dean-Stark trap, a mixture of pyridoxal hydrochloride (330 mg, 1.62 mmol), 4'-amino-biphenyl-2-sulfonic acid tert-butylamide (494 mg, 1.62 mmol), p-toluenesulfonic acid monohydrate (68 mg, 0.36 mmol) in toluene (150 mL) was heated at 100° C. under nitrogen atmosphere for 3 hours. The solvent was then evaporated and the crude product was dissolved in dichloromethane (70 mL), cooled down to 0° C. and then sodium borohydride (163 mg, 4.32 mmol) and methyl alcohol (15 mL) were added. The reaction mixture was stirred at room temperature overnight, after which the solvent was removed. The residue was diluted with saturated aqueous sodium bicarbonate and extracted with ethyl acetate. The organic layer was dried over anhydrous magnesium sulfate, filtered and evaporated. The crude product was purified by column chromatography on silica gel using a mixture of dichloromethane:methyl alcohol (9:1) as eluant to give 4'-[(3hydroxy-5-hydroxymethyl-2-methyl-pyridin-4-ylmethyl)-amino]-biphenyl-2-sulfonic acid tert-butylamide (7) (178 mg, 24% overall yield for two steps) as a colorless solid.

$^1$H-NMR (CDCl$_3$): δ 8.13 (dd, 1H), 7.84 (s, 1H), 7.53 (td, 1H), 7.44 (td, 1H), 7.37 (d, 2H), 7.27 (dd, 1H), 6.89 (d, 2H), 4.68 (s, 2H), 4.61 (s, 2H), 3.71 (s, 1H), 2.44 (s, 3H), 0.98 (s, 9H). MS m/z (ES$^+$): 456.29 (M+H$^+$).

Example 8

Synthesis of 4'-[(3-Hydroxy-5-hydroxymethyl-pyridin-4-ylmethyl)-amino]-biphenyl-2-sulfonic acid amide (8)

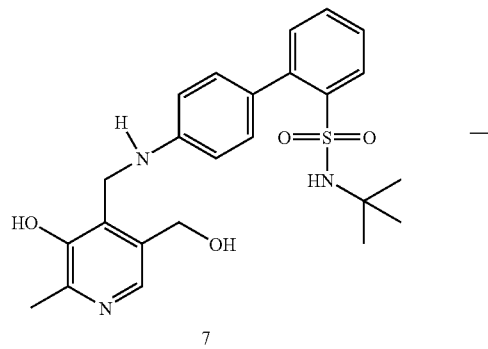

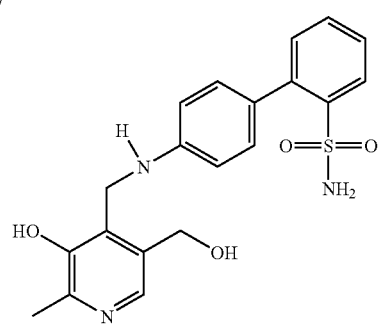

The hydrolysis of 4'-[(3-hydroxy-5-hydroxymethyl-2-methyl-pyridin-4-ylmethyl)-amino]-biphenyl-2-sulfonic acid tert-butylamide (7) (75 mg, 0.16 mmol), following the procedure described in Example 3, gave 4'-[(3-hydroxy-5-hydroxymethyl-pyridin-4-ylmethyl)-amino]-biphenyl-2-sulfonic acid amide (8) (49 mg, 76% yield) as a colorless solid.

$^1$H-NMR (CD$_3$OD): δ 8.09 (s, 1H), 7.92 (dd, 1H), 7.45-7.38 (m, 2H), 7.28 (dt, 2H), 7.16-7.10 (m, 3H), 4.70 (s, 2H), 4.66 (s, 2H), 2.53 (s, 3H). MS m/z (ES$^+$): 400.28 (M+H$^+$).

Example 9

Synthesis of 3'-Fluoro-4'-[(3-hydroxy-5-hydroxymethyl-2-methyl-pyridin-4-ylmethyl)-amino]-biphenyl-2-sulfonic acid tert-butylamide (9)

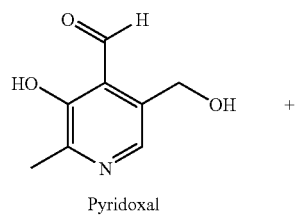

Pyridoxal

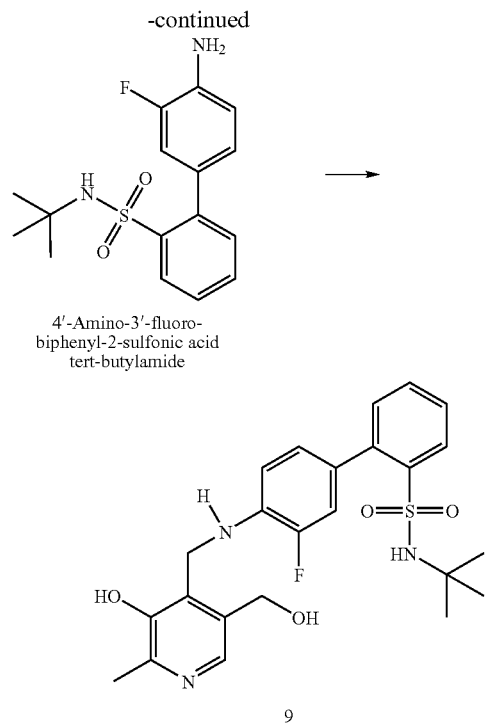

4'-Amino-3'-fluoro-biphenyl-2-sulfonic acid tert-butylamide

9

The reductive amination of pyridoxal hydrochloride (436.4 mg, 2.143 mmol) and 4'-amino-3'-fluoro-biphenyl-2-sulfonic acid tert-butylamide (760 mg, 2.357 mmol), following the procedure described in Example 7, gave 3'-fluoro-4'-[(3-hydroxy-5-hydroxymethyl-2-methyl-pyridin-4-ylmethyl)-amino]-biphenyl-2-sulfonic acid tert-butylamide (9).

Example 10

Synthesis of N-tert-Butyl-2-[6-(2,2,8-trimethyl-4H-[1,3]dioxino[4,5-c]pyridin-5-ylamino)-pyridin-3-yl]-benzenesulfonamide (11)

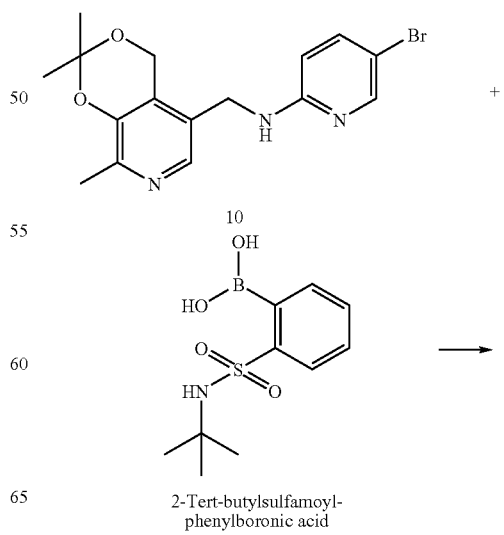

2-Tert-butylsulfamoyl-phenylboronic acid

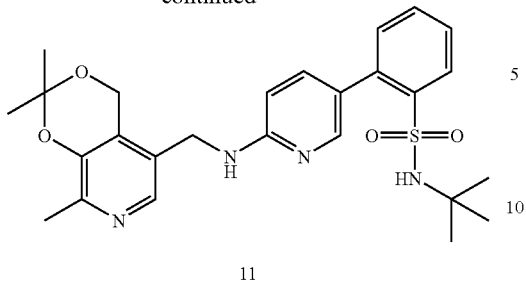

11

A mixture of (5-bromo-pyridin-2-yl)-(2,2,8-trimethyl-4H-[1,3]dioxino[4,5-c]pyridin-5-yl)-amine (10) (564 mg, 1.55 mmol), tetrakis(triphenylphosphine) palladium(0) (174 mg, 0.15 mmol), cesium carbonate (1.56 g, 4.8 mmol), 2-tert-butylsulfamoyl-phenylboronic acid (438 mg, 1.7 mmol) in a solution of toluene (20 mL), iso-butyl alcohol (15 mL) and water (5 mL) was stirred at 80° C. under nitrogen for 5 h. The reaction was diluted with water and extracted with ethyl ether. The organic layer was dried over anhydrous magnesium sulfate, filtered and evaporated. The crude product was purified by column chromatography on silica gel to give N-tert-butyl-2-[6-(2,2,8-trimethyl-4H-[1,3]dioxino[4,5-c]pyridin-5-ylamino)-pyridin-3-yl]-benzenesulfonamide (11) as a colorless solid (554 mg, 74% yield).

$^1$H-NMR (CDCl$_3$): δ 8.15 (d, 1H), 8.10 (s, 1H), 8.03 (s, 1H), 7.68 (d, 1H), 7.55 (t, 1H), 7.46 (t, 1H), 7.27 (d, 1H), 6.47 (d, 1H), 4.91 (s, 2H), 4.84 (t, 1H), 4.44 (d, 2H), 3.76 (s, 1H), 2.40 (s, 3H), 1.55 (s, 6H), 1.03 (s, 9H).

Example 11

Synthesis of N-tert-Butyl-2-[6-(5-hydroxy-4-hydroxymethyl-6-methyl-pyridin-3-ylamino)-pyridin-3-yl]-benzenesulfonamide (12)

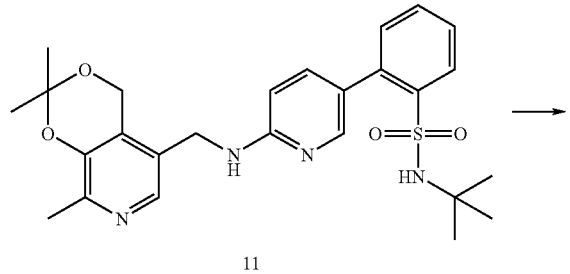

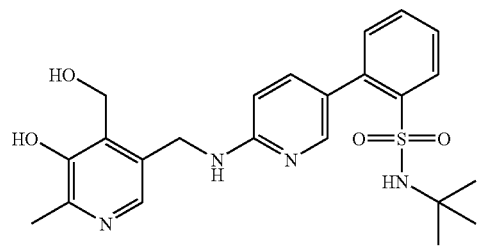

12

The hydrolysis of N-tert-butyl-2-[6-(2,2,8-trimethyl-4H-[1,3]dioxino[4,5-c]pyridin-5-ylamino)-pyridin-3-yl]-benzenesulfonamide (12) (305 mg, 0.63 mmol), following the procedure described in Example 2, gave N-tert-butyl-2-[6-(5-hydroxy-4-hydroxymethyl-6-methyl-pyridin-3-ylamino)-pyridin-3-yl]-benzenesulfonamide (12) (244 mg, 84% yield) as a colorless solid.

$^1$H-NMR (CD$_3$OD): δ 8.13-8.10 (m, 3H), 7.97 (d, 2H), 7.64-7.60 (m, 2H), 7.52 (t, 1H), 7.34 (d, 1H), 6.69 (d, 1H), 5.02 (s, 2H), 4.59 (s, 2H), 2.46 (s, 3H), 1.06 (s, 9H).

Example 12

Synthesis of 4'-{[5-(3-Cyano-benzyloxy)-4-hydroxymethyl-6-methyl-pyridin-3-ylmethyl]-amino}-biphenyl-2-sulfonic acid tert-butylamide (13)

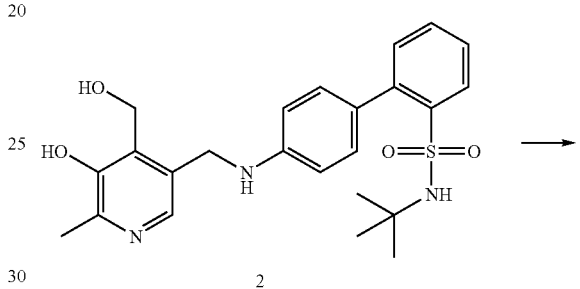

2

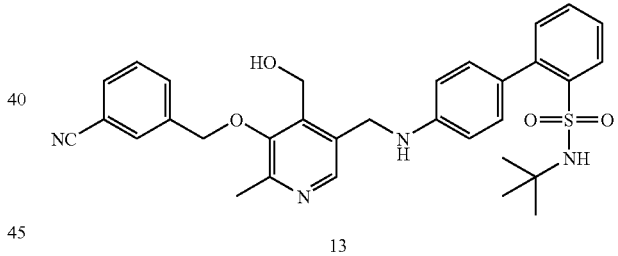

13

A mixture of 4'-[(5-hydroxy-4-hydroxymethyl-6-methyl-pyridin-3-ylmethyl)-amino]-biphenyl-2-sulfonic acid tert-butylamide (2) (190 mg, 0.42 mmol), α-bromo-m-tolunitrile (90 mg, 0.46 mmol) and potassium carbonate (177 mg, 1.28 mmol) in DMF (10 mL) were stirred at room temperature under nitrogen atmosphere overnight. The reaction mixture was evaporated to dryness, and the crude product was purified by column chromatography on silica gel using a gradient of dichloromethane:methyl alcohol (1:0 to 9:1) as eluant to give 4'-{[5-(3-cyano-benzyloxy)-4-hydroxymethyl-6-methyl-pyridin-3-ylmethyl]-amino}-biphenyl-2-sulfonic acid tert-butylamide (13) (149 mg, 62% yield) as a colorless solid.

$^1$H-NMR (CDCl$_3$): δ 8.39 (s, 1H), 8.16 (d, 1H), 7.83 (s, 1H), 7.75-7.68 (m, 2H), 7.59-7.53 (m, 2H), 7.49-7.41 (m, 3H), 7.31 (d, 2H), 6.87 (d, 2H), 5.03 (s, 2H), 4.81 (s, 2H), 4.46 (s, 2H), 3.70 (s, 1H), 2.58 (s, 3H), 1.02 (s, 9H).

Example 13

Synthesis of 3-{4-Hydroxymethyl-5-[(2'-sulfamoyl-biphenyl-4-ylamino)-methyl]-pyridin-3-yloxymethyl}-benzamidine (14)

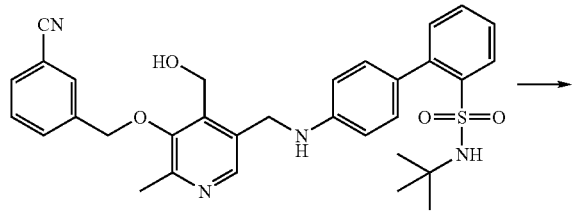

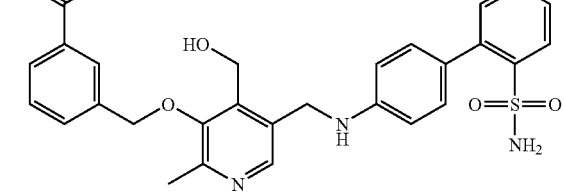

Hydrogen chloride gas was bubbled into a suspension of 4'-{[5-(3-cyano-benzyloxy)-4-hydroxymethyl-6-methyl-pyridin-3-ylmethyl]-amino}-biphenyl-2-sulfonic acid tert-butylamide (13) (100 mg, 0.17 mmol) in absolute ethyl alcohol (30 mL) at 0° C. for 30 minutes. The septum was replaced and the reaction mixture was stirred at room temperature overnight. Hydrogen chloride gas was purged with nitrogen gas for 2 hours and the solvent evaporated to give the crude amide ester as a solid. Ammonia in methyl alcohol (30 mL, 7 M, 350 mmol) was added to the crude amide ester and the reaction mixture was stirred overnight at room temperature. The solvent was evaporated and the product purified on a silica gel column using a mixture of dichloromethane:methyl alcohol (4:1) as eluant to give the corresponding 3-{4-hydroxymethyl-5-[(2'-sulfamoyl-biphenyl-4-ylamino)-methyl]-pyridin-3-yloxymethyl}-benzamidine (14) (90 mg, 97% yield) as a colorless powder.

$^1$H-NMR (CD$_3$OD): δ 8.30 (s, 1H), 8.07 (d, 1H), 8.01 (s, 1H), 7.92 (d, 1H), 7.84 (d, 1H), 7.70 (t, 1H) 7.58 (t, 1H), 7.46 (t, 1H), 7.32 (d, 1H), 7.24 (d, 2H), 6.77 (d, 2H), 5.11 (s, 2H), 4.58 (s, 2H), 3.36 (s, 2H), 2.52 (s, 3H). MS m/z (ES$^+$): 532.37 (M+H$^+$).

Example 14

Synthesis of N-tert-Butyl-2-{6-[3-(3-cyano-benzyloxy)-2-hydroxymethyl-4-methyl-benzylamino]-pyridin-3-yl}-benzenesulfonamide (15)

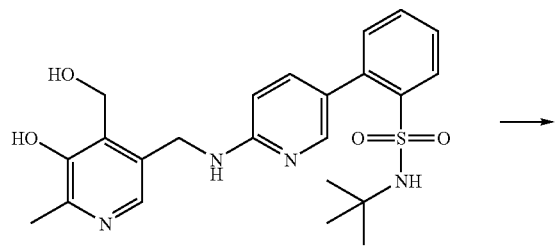

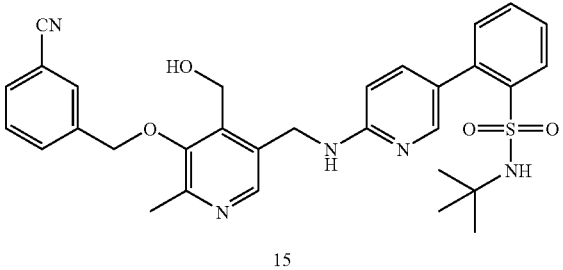

The coupling of N-tert-butyl-2-[6-(5-hydroxy-4-hydroxymethyl-6-methyl-pyridin-3-ylamino)-pyridin-3-yl]-benzenesulfonamide (12) (205 mg, 0.45 mmol) and α-bromo-m-tolunitrile (88 mg, 0.45 mmol), following the procedure described in Example 12, gave N-tert-butyl-2-{6-[3-(3-cyano-benzyloxy)-2-hydroxymethyl-4-methyl-benzylamino]-pyridin-3-yl}-benzenesulfonamide (15) (23 mg, 9% yield).

$^1$H-NMR (CDCl$_3$): δ 8.38 (s, 1H), 8.14 (dd, 1H), 7.98 (d, 1H), 7.81 (s, 1H), 7.74-7.64 (m, 3H), 7.55-7.46 (m, 3H), 7.24 (dd, 1H), 6.56 (d, 1H), 5.35 (t, 1H), 4.99 (s, 2H), 4.85 (s, 2H), 4.71 (d, 2H), 3.63 (s, 1H), 2.51 (s, 3H), 1.00 (s, 9H).

Example 15

Synthesis of 3-(2-Hydroxymethyl-6-methyl-3-{[5-(2-sulfamoyl-phenyl)-pyridin-2-ylamino]-methyl}-phenoxymethyl)-benzamidine (16)

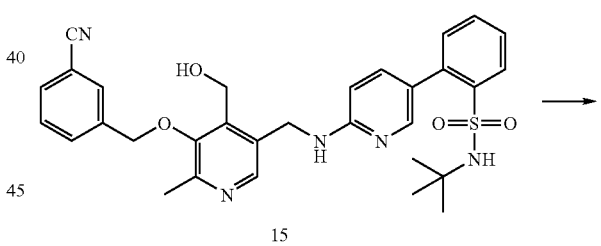

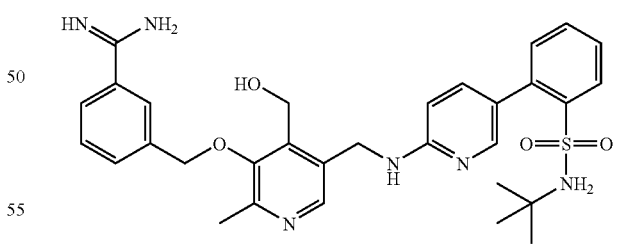

The conversion of nitrile (15) to amidine (16) was carried out as described in Example 13.

$^1$H-NMR (CD$_3$OD): δ 8.32 (s, 1H), 8.11 (dd, 1H), 8.01 (t, 1H), 7.96 (d, 1H), 7.92 (d, 1H), 7.83 (d, 1H), 7.69 (t, 1H), 7.64-7.50 (m, 3H), 7.32 (dd, 1H), 6.67 (d, 1H), 5.12 (s, 2H), 4.88 (s, 2H), 4.73 (s, 2H), 2.52 (s, 3H). MS m/z (ES$^+$): 533.42 (M+H$^+$).

Example 16

Synthesis of 4'-{[5-(3-Cyano-benzyloxy)-4-hydroxymethyl-6-methyl-pyridin-3-ylmethyl]-amino}-biphenyl-2-sulfonic acid tert-butylamide (17)

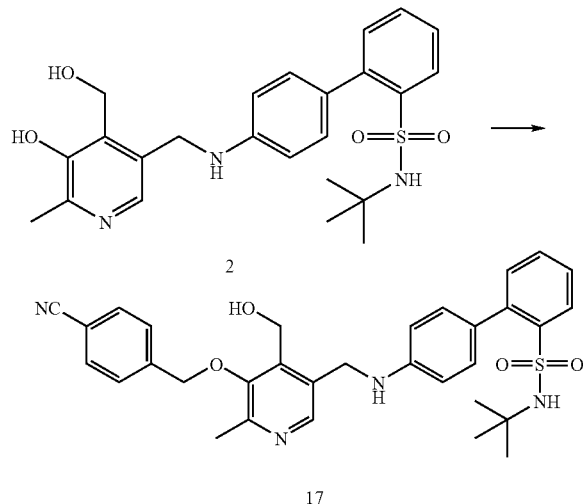

The coupling of 4'-[(5-hydroxy-4-hydroxymethyl-6-methyl-pyridin-3-ylmethyl)-amino]-biphenyl-2-sulfonic acid tert-butylamide (2) (190 mg, 0.42 mmol) and α-bromo-p-tolunitrile (90 mg, 0.46 mmol), following the procedure described in Example 12, gave 4'-{[5-(3-cyano-benzyloxy)-4-hydroxymethyl-6-methyl-pyridin-3-ylmethyl]-amino}-biphenyl-2-sulfonic acid tert-butylamide (58) (149 mg, 62% yield) as a colorless solid.

$^1$H-NMR (CDCl$_3$): δ 8.39 (s, 1H), 8.16 (d, 1H), 7.83 (s, 1H), 7.75-7.68 (m, 2H), 7.59-7.53 (m, 2H), 7.49-7.41 (m, 3H), 7.31 (d, 2H), 6.87 (d, 2H), 5.03 (s, 2H), 4.81 (s, 2H), 4.46 (s, 2H), 3.70 (s, 1H), 2.58 (s, 3H), 1.02 (s, 9H).

Example 17

Synthesis of 3-{4-Hydroxymethyl-5-[(2'-sulfamoyl-biphenyl-4-ylamino)-methyl]-pyridin-3-yloxymethyl}-benzamidine (18)

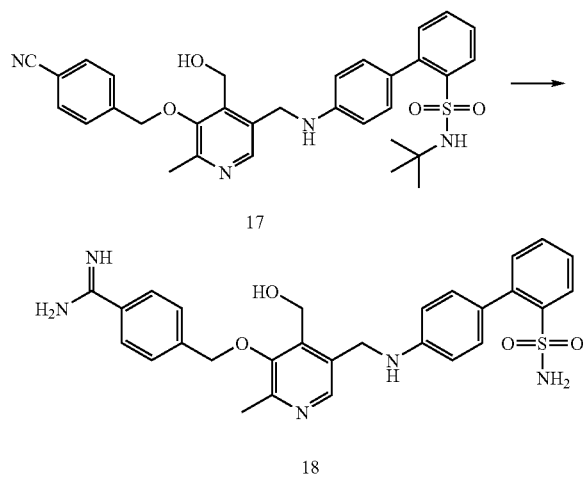

The conversion of nitrile (17) to amidine (18) was carried out as described in Example 13.

$^1$H-NMR (CD$_3$OD): δ 8.30 (s, 1H), 8.07 (d, 1H), 8.01 (s, 1H), 7.92 (d, 1H), 7.84 (d, 1H), 7.70 (t, 1H) 7.58 (t, 1H), 7.46 (t, 1H), 7.32 (d, 1H), 7.24 (d, 2H), 6.77 (d, 2H), 5.11 (s, 2H), 4.58 (s, 2H), 3.36 (s, 2H), 2.52 (s, 3H). MS m/z (ES$^+$): 532.37 (M+H$^+$).

Example 18

Inhibition of Platelet Aggregation

Platelet rich plasma (PRP) was obtained by drawing whole blood from normal human donors (not on any medication) into sodium citrate tubes (3.2%), and centrifuging at 160 xg for about 10 minutes. Platelet poor plasma (PPP) was obtained by centrifuging the remainder of the sample after the platelets were removed at 800 g for about 10 minutes. The PRP was adjusted to a count of 280×10$^9$/L using a mixture of PRP and PPP. The platelets (200 μL) were incubated with the test compounds (25 μL) adjusted to various concentrations 250 μM for about 30 minutes at room temperature (approximate final platelet count in the incubation mixture of 250×10$^9$/L). The samples were incubated for about 3 minutes at about 37° C., and then transferred to the mixing wells of a Chrono-log 4 channel aggregometer (Chrono-log Corp., Havertown, Pa.). After baselines were established, the agonist (25 μL of 40 μM ADP (Sigma, St. Louis, Mo.) or 25 μL of 50 μg/mL and 10 μg/mL collagen (Helena Laboratories, Beaumont, Tex.) or 25 μL of 120 μM thrombin receptor activating peptide (TRAP) (Sigma)) was then added. Aggregation was monitored for 5 minutes at 37° C. with stirring (1000 rpm). The amplitude and slope of each tracing were calculated to determine the amount of aggregation. Control samples were performed using only solvent. The % reduction in aggregation was calculated for each sample compared to the proper solvent control. See Table 1.

TABLE 1

| | | Platelet inhibition | | | |
| --- | --- | --- | --- | --- | --- |
| | | % Reduction in Aggregation | | | |
| Compound | Concentration (μM) | Collagen (5 μg/mL) | Collagen (1 μg/mL) | ADP (4 μM) | TRAP (12 μM) |
| 3 | 250 | 5 | 0 | 0 | 6 |
| 6 | 250 | 0 | 4 | 14 | 0 |
| 18 | 250 | 9 | 23 | 50 | 74 |
| 14 | 250 | 5 | 15 | 10 | 9 |
| 16 | 250 | 0 | 14 | 3 | 1.3 |

The invention claimed is:
1. A compound of the formula:

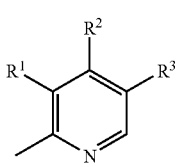

wherein
A)
R$^1$ is —OH; —O-alkyl; —(CH$_2$)$_n$OH where n' is an integer from 1 to 8; alkyl; cycloalkyl; or O-alkyl-aryl-R$^4$, where R$^4$ is —CN or amidine;

$R^2$ is $(CH_2)_n$-aryl-$R^5$ where n is an integer from 0 to 8 and $R^5$ is $SO_2NH_2$ or $SO_2NHC(CH_3)_3$; $(CH_2)_n$-aryl-aryl-$R^5$, where n and $R^5$ are as defined above, or —$(CH_2)_n$—NH-aryl-$R^5$, where n and $R^5$ are as defined above; and $R^3$ is —$(CH_2)_n$OH where n is as defined above; $(CH_2)_n$—NH-aryl-$R^5$, where n and $R^5$ are as defined above; $(CH_2)_n$—NH—CO-aryl-$R^5$ where n and $R^5$ are as defined above; $(CH_2)_n$—NH-aryl-aryl-$R^5$ where n and $R^5$ are as defined above; or $(CH^2)_n$—NH—CO-aryl-$R^5$ where n and $R^5$ are as defined above; or B)
$R^1$ is —OH; —O-alkyl; —$(CH_2)_{n'}$OH where n' is an integer from 1 to 8; alkyl; cycloalkyl; or O-alkyl-aryl-$R^4$, where $R^4$ is —CN or amidine;

$R^2$ is alkyl; —$(CH_2)_{n'}$OH where n' is as defined above; —$(CH_2)_n$COOH where n is an integer from 0 to 8; —$(CH_)_n^2$COO$(CH_2)_n$CH$_3$ where n is as defined above; $(CH^2)_n$-aryl-$R^5$ where n is as defined above and $R^5$ is $SO_2NH_2$ or $SO_2NHC(CH_3)_3$; $(CH_2)_n$-aryl-aryl-$R^5$, where n and $R^5$ are as defined above, or —$(CH_2)_n$-NH-aryl-$R^5$, where n and $R^5$ are as defined above;

$R^3$ is $(CH_2)_n$—NH-aryl-$R^5$, where n and $R^5$ are as defined above; $(CH_2)_n$—NH—CO-aryl-$R^5$ where n and $R^5$ are as defined above; $(CH_2)_n$—NH-aryl-aryl-$R^5$ where n and $R^5$ are as defined above; or $(CH^2)_n$—NH—CO-aryl-aryl-$R^5$ where n and $R^5$ are as defined above and
$R^1$ and $R^2$ when taken together form a compound of formula II,

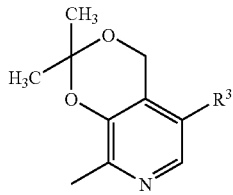

wherein $R^3$ is as defined above;
or a pharmaceutically acceptable salt thereof.

2. The compound of claim 1, wherein an alkyl is substituted with one or more of fluorine, chlorine, alkoxy groups having 1 to 8 carbon atoms, or amido groups having from 1 to 8 carbon atoms.

3. The compound of claim 2, wherein the alkoxy group is methoxy or ethoxy.

4. The compound of claim 2, wherein the amido group is acetamido.

5. The compound of claim 1, wherein an aryl group is a phenyl group or a naphthyl group.

6. The compound of claim 1, wherein an aryl group is substituted with one or more of fluorine, chlorine, bromine, alkyl groups having 1 to 8 carbon atoms, alkoxy groups having 1 to 8 carbon atoms, alkoxyalkyl groups having 1 to 8 carbon atoms, or amido groups having 1 to 8 carbon atoms.

7. The compound of claim 6, wherein the alkyl group is methyl or ethyl.

8. The compound of claim 6, wherein the alkoxy group is methoxy or ethoxy.

9. The compound of claim 6, wherein the amido group is acetamido.

10. The compound of claim 1, wherein an aryl group is substituted with one or more functional groups.

11. The compound of claim 10, wherein the functional group is a hydroxy group, carboxy group, or acetoxy group.

12. A compound of the formula

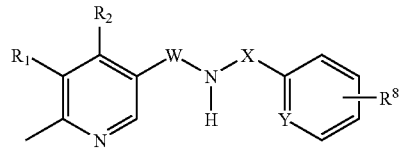

wherein
$R^1$ is OH, OCH$_3$, or OCH$_2$—(4-tert-Butyl-phenyl), or

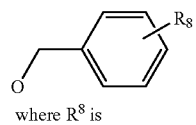

where $R^8$ is

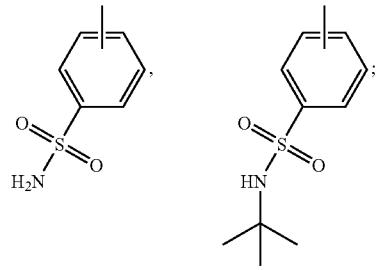

$R^2$ is CH$_2$OH or

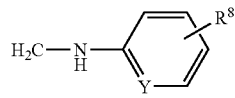

where $R^8$ is as defined above;
W is $(CH_2)_{n'}$ where n'=1, 2 or 3;
X is $(CH_2)_n$ where n=0, 1, 2, or 3, or C=O;
Y is C—H, C—F, or N; and
$R^1$ and $R^2$ when taken together form a compound of formula

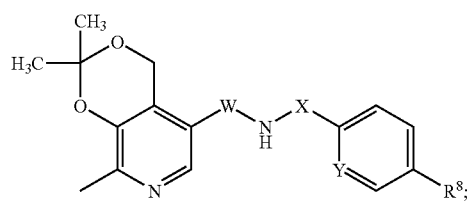

or a pharmaceutically acceptable salt thereof.

13. The compound of claim 12, wherein the compound is 3-{4-Hydroxymethyl-5[(2'-sulfamoyl-biphenyl-4-ylaminomethyl]-pyridin-3-yloxymethyl}-benzamidine.

14. A method of inhibiting platelet aggregation comprising administering the compound of claim 1.

15. The method of claim 14, wherein said compound is administered enterally, parenterally, or by inhalation.

16. A method of inhibiting platelet aggregation comprising administering the compound of claim 12.

17. The method of claim 16, wherein the compound is 3-{4-Hydroxymethyl-5[(2'-sulfamoyl-biphenyl-4-ylaminomethyl]-pyridin-3-yloxymethyl}-benzamidine.

18. The method of claim 15, wherein the compound is administered concurrently with another therapeutic agent.

19. The method of claim 18, wherein said other therapeutic agent is an anti-platelet agent, glycoprotein IIb/IIIa inhibitor, or anticoagulant.

20. The method of claim 19, wherein said anti-platelet agent is clopidogrel, aspirin, or dipyridamole.

21. The method of claim 19, wherein said glycoprotein IIb/IIIa inhibitor is eptifibatide.

22. The method of claim 19, wherein said anticoagulant is unfractionated heparin, low molecular weight heparins, hirudin, or argatroban.

23. A method of inhibiting platelet aggregation in a mammal post-surgically comprising administering a therapeutically effective amount of the compound according to claim 1 following a surgical procedure.

24. A method of claim 23, wherein the surgical procedure is a hip replacement, invasive cardiovascular surgery, or angioplasty.

25. A method of claim 24 wherein the invasive cardiovascular surgery is coronary artery bypass graft or heart valve replacement.

26. A method of claim 23, wherein the angioplasty is coronary, pulmonary, peripheral, intracranial, extracranial carotid, renal, and aortic angioplasty.

27. The method of claim 23, wherein the compound is administered concurrently with another therapeutic agent.

28. The method of claim 23, wherein the compound is coated on a medical device.

29. The method of claim 28, wherein the medical device is an intravascular stent or catheter.

30. A method of inhibiting platelet aggregation in a mammal post-surgically comprising administering a therapeutically effective amount of the compound according to claim 12 following a surgical procedure.

31. A method of claim 30, wherein the surgical procedure is a hip replacement angioplasty, or invasive cardiovascular surgery.

32. A method of claim 31, wherein the invasive cardiovascular surgery is coronary artery bypass graft or heart valve replacement.

33. A method of claim 31, wherein the angioplasty is coronary, pulmonary, peripheral, intracranial, extracranial carotid, renal, and aortic angioplasty.

34. The method of claim 30, wherein the compound is administered concurrently with another therapeutic agent.

35. The method of claim 30, wherein the compound is coated on a medical device.

36. The method of claim 35, wherein the medical device is an intravascular stent or catheter.

* * * * *

UNITED STATES PATENT AND TRADEMARK OFFICE
CERTIFICATE OF CORRECTION

PATENT NO. : 7,459,468 B2  Page 1 of 1
APPLICATION NO. : 10/974707
DATED : December 2, 2008
INVENTOR(S) : Haque et al.

It is certified that error appears in the above-identified patent and that said Letters Patent is hereby corrected as shown below:

Col. 3, line 45: " 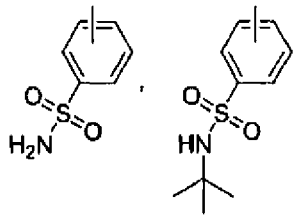 " should read -- 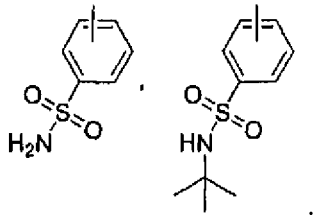 ;--

Col. 26, line 18: "800 g" should read --800 $x$g--

Signed and Sealed this

Twenty-fourth Day of March, 2009

JOHN DOLL
*Acting Director of the United States Patent and Trademark Office*